(12) United States Patent
Chapman et al.

(10) Patent No.: US 8,466,284 B2
(45) Date of Patent: Jun. 18, 2013

(54) SOME 2-PYRAZINONE DERIVATIVES AND THEIR USE AS INHIBITORS OF NEUTROPHILE ELASTASE

(75) Inventors: David Chapman, Lund (SE); Martin Lindsjö, Lund (SE); Hans Lönn, Lund (SE); Michael Lundkvist, Lund (SE); Magnus Munck AF Rosenschöld, Lund (SE); Antonios Nikitidis, Lund (SE); Debra Ainge, Leicestershire (GB); John Pavey, Leicestershire (GB)

(73) Assignee: Astra Zeneca AB, Sodertalje (SE)

( * ) Notice: Subject to any disclaimer, the term of this patent is extended or adjusted under 35 U.S.C. 154(b) by 188 days.

(21) Appl. No.: 12/740,136

(22) PCT Filed: Nov. 5, 2008

(86) PCT No.: PCT/SE2008/051263
§ 371 (c)(1),
(2), (4) Date: Jul. 19, 2010

(87) PCT Pub. No.: WO2009/061271
PCT Pub. Date: May 14, 2009

(65) Prior Publication Data
US 2010/0280048 A1    Nov. 4, 2010

Related U.S. Application Data

(60) Provisional application No. 60/985,713, filed on Nov. 6, 2007.

(51) Int. Cl.
*C07D 241/02* (2006.01)
(52) U.S. Cl.
USPC .................................. 544/408; 548/377.1
(58) Field of Classification Search
USPC .................................. 544/408; 548/377.1
See application file for complete search history.

(56) References Cited

U.S. PATENT DOCUMENTS

| | | | |
|---|---|---|---|
| 4,181,658 A | 1/1980 | Hitzel et al. |
| 4,186,200 A | 1/1980 | Kubo et al. |
| 5,441,960 A | 8/1995 | Bernstein et al. |
| 5,521,179 A | 5/1996 | Bernstein et al. |
| 6,028,081 A | 2/2000 | Sada et al. |
| 6,977,266 B2 | 12/2005 | Tada et al. |
| 6,979,690 B2 | 12/2005 | Gymer et al. |
| 7,629,362 B2 | 12/2009 | Mitsuya et al. |
| 2004/0023973 A1 | 2/2004 | Nagato et al. |
| 2004/0082619 A1 | 4/2004 | Tada et al. |
| 2004/0235761 A1 | 11/2004 | Furuta et al. |
| 2005/0101590 A1 | 5/2005 | Yasui et al. |
| 2006/0035938 A1 | 2/2006 | Bladh et al. |
| 2006/0052411 A1 | 3/2006 | Tada et al. |
| 2006/0100249 A1 | 5/2006 | Smith |
| 2006/0211695 A1 | 9/2006 | Borzilleri et al. |
| 2006/0270666 A1 | 11/2006 | Bladh et al. |
| 2007/0010551 A1 | 1/2007 | Bladh et al. |
| 2007/0043036 A1 | 2/2007 | Hansen et al. |
| 2007/0203129 A1 | 8/2007 | Andersson et al. |
| 2007/0213323 A1 | 9/2007 | Imogai et al. |
| 2008/0103139 A1 | 5/2008 | Ishizuka et al. |
| 2009/0105239 A1 | 4/2009 | Brimert et al. |
| 2009/0131483 A1 | 5/2009 | Hansen et al. |
| 2009/0131486 A1 | 5/2009 | Hansen et al. |
| 2009/0209539 A1 | 8/2009 | Leblanc et al. |
| 2009/0209555 A1 | 8/2009 | Hansen et al. |
| 2010/0216843 A1 | 8/2010 | Briggner et al. |
| 2010/0280048 A1 | 11/2010 | Ainge et al. |

FOREIGN PATENT DOCUMENTS

| | | |
|---|---|---|
| EP | 0008864 A1 | 3/1980 |
| EP | 1300396 A1 | 4/2003 |
| EP | 1357111 A1 | 10/2003 |
| EP | 1598349 A1 | 11/2005 |
| EP | 1806342 A1 | 7/2007 |
| GB | 2383326 A | 6/2003 |
| GB | 2392910 A | 3/2004 |
| JP | 2152966 A | 6/1990 |
| WO | WO-98/24780 A2 | 6/1998 |
| WO | WO-01/96308 A1 | 12/2001 |
| WO | WO-02/053543 A1 | 7/2002 |

(Continued)

OTHER PUBLICATIONS

U.S. Appl. No. 12/895,995, Muragan et al.
Opposition to a Patent of Invention, Costa Rican Patent File No. 11416, published in the Gazette on Aug. 31, 2010 (3rd publication).
Eistert, B., et al., "Reactions of quinones and α-dicarbonyl compounds with diazoalkanes, XXIV. Synthesis and reactions of substituted pyrroline-2,3-diones with diazoalkanes," *Liebigs Ann. Chem.* (1976), vol. 6, pp. 1023-1030.
Office Action dated Apr. 9, 2008 in U.S. Appl. No. 10/569,923.
Office Action dated Dec. 12, 2008 in U.S. Appl. No. 10/569,923.

(Continued)

*Primary Examiner* — Douglas M Willis
(74) *Attorney, Agent, or Firm* — Kate Kizer

(57) ABSTRACT

The invention provides certain novel compounds as listed in the specification and pharmaceutically acceptable salts thereof and particular Forms thereof; together with processes for their preparation, pharmaceutical compositions containing them and their use in therapy. The compounds are inhibitors of human neutrophil elastase. The present neutrophil elastase inhibitors include 6-[1-(4-Cyanophenyl)-1H-pyrazol-5-yl]-5-methyl-3-oxo-4-[3-(trifluoromethyl)phenyl]-3, 4-dihydropyrazine-2-carboxamide:

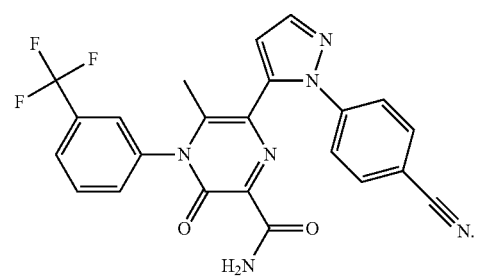

19 Claims, 3 Drawing Sheets

FOREIGN PATENT DOCUMENTS

| | | |
|---|---|---|
| WO | WO-03/015798 A1 | 2/2003 |
| WO | WO-03/047577 A2 | 6/2003 |
| WO | WO-03/070277 A1 | 8/2003 |
| WO | WO-2004/020410 A2 | 3/2004 |
| WO | WO-2004/043924 A1 | 5/2004 |
| WO | WO-2004/081001 A1 | 9/2004 |
| WO | WO-2005/021509 A1 | 3/2005 |
| WO | WO-2005/021512 A1 | 3/2005 |
| WO | WO-2005/026123 A1 | 3/2005 |
| WO | WO-2005/026124 A1 | 3/2005 |
| WO | WO-2005/080372 A1 | 9/2005 |
| WO | WO-2005/082864 A1 | 9/2005 |
| WO | WO-2006/004636 A2 | 1/2006 |
| WO | WO-2006/030032 A1 | 3/2006 |
| WO | WO-2006/046778 A1 | 5/2006 |
| WO | WO-2006/082412 A2 | 8/2006 |
| WO | WO-2006/098683 A1 | 9/2006 |
| WO | WO-2006/098684 A1 | 9/2006 |
| WO | WO-2006/116713 A1 | 11/2006 |
| WO | WO-2006/136857 A1 | 12/2006 |
| WO | WO-2007/107706 A2 | 9/2007 |
| WO | WO-2007/129060 A1 | 11/2007 |
| WO | WO-2007/129962 A1 | 11/2007 |
| WO | WO-2007/129963 A1 | 11/2007 |
| WO | WO-2008/006583 A1 | 1/2008 |
| WO | WO-2008/030158 A1 | 3/2008 |
| WO | WO-2008/104752 A1 | 9/2008 |
| WO | WO-2009/058076 A1 | 5/2009 |
| WO | WO-2009/061271 A1 | 5/2009 |
| WO | WO-2010/094964 A1 | 8/2010 |

OTHER PUBLICATIONS

Restriction Requirement dated Feb. 28, 2008 in U.S. Appl. No. 10/534,720.
Office Action dated Jun. 23, 2008 in U.S. Appl. No. 10/534,720.
Office Action dated Jan. 2, 2008 in U.S. Appl. No. 10/534,720.
Interview Summary dated Jul. 14, 2009 in U.S. Appl. No. 10/534,720.
Office Action dated Sep. 29, 2008 in U.S. Appl. No. 10/569,571.
Office Action dated Mar. 16, 2009 in U.S. Appl. No, 10/569,571.
Interview Summary dated Sep. 28, 2009 in U.S. Appl. No. 10/569,571.
Restriction dated Jan. 21, 2009 in U.S. Appl. No. 10/572,640.
Interview Summary dated Aug. 4, 2009 in U.S. Appl. No. 10/572,640.
Restriction dated Aug. 25, 2009 in U.S. Appl. No. 12/299,879.
Office Action dated Dec. 28, 2009 in U.S. Appl. No. 12/299,879.
Office Action dated Jun. 24, 2010 in U.S. Appl. No. 12/299,879.
Notice of Allowance and Interview Summary dated Sep. 23, 2010 in U.S. Appl. No. 12/299,879.
Restriction dated Oct. 29, 2009 in U.S. Appl. No. 10/572,706.
Office Action dated Feb. 17, 2010 in U.S. Appl. No. 10/572,706.
Ex-parte Quayle Action dated Jul. 21, 2010 in U.S. Appl. No. 10/572,706.
Notice of Allowance dated Nov. 5, 2010 in U.S. Appl. No. 10/572,706.
Interview Summary dated Nov. 5, 2010 in U.S. Appl. No. 10/572,706.
Oyedo, et al., Opposition to Chilean Patent Application No. 3301-2008, Published Oct. 16, 2009.
Bauer, A., et al., "Benzodiazepines with Psychotropic Activity, V[1])—1,5-Benzodiazepinetriones and Their Precursors", *Liebings Ann. Chem.*, vol. 762, pp. 73-82 (1972).
Chughtai, B., et al., "Potential Role of Inhibitors of Neutrophil Elastase in Treating Diseases of the Airway", *Journal of Aerosol Medicine*, vol. 17 (6), pp. 289-298 (2004).
Friedman, M., "Future Treatment Strategies for COPD", *clinical CORNERSTONE—COPD*, vol. 5 (1), pp. 45-51 (2004).
Ohbayashi, H., "Current Synthetic Inhibitors of Human Neutrophil Elastase in 2005", *Expert Opin. Ther. Patents*, vol. 15 (7), pp. 759-771 (2005).
Ohbayashi, H., "Novel Neutrophil Elastase Inhibitors as a Treatment for Neutrophil-Predominant Inflammatory Lung Diseases", *The Investigational Drugs Journal*, vol. 5 (9), pp. 910-923 (2002).
Ohbayashi, H., "Neutrophil Elastase inhibitors as Treatment for COPD", *Expert Opinion on Investigational Drugs*, vol. 11 (7), pp. 965-980 (2002).
Okayama, N., et al., "Clinical Effects of a Neutrophil Elastase Inhibitor, Sivelestat, in Patients with Acute Respiratory Distress Syndrome", *Journal of Anesthesia*, vol. 20, pp. 6-10, (2006).
Sato, T., et al., "Neutrophil Elastase and Cancer", *Surgical Oncology*, vol. 15, pp. 217-222 (2006).
Shimizu, T., et al., "A Mechanism of Antigen-Induced Mucus Production in Nasal Epithelium of Sensitized Rats", *Am. J. Respir. Crit. Care Med.*, vol. 161 (5), pp. 1648-1654 (2000).
Ukrainets, I.V., et al., "4-Hydroxy-2-Quinolones, 23. N-(2-Thiazolyl)Amides of 1-R-2-Oxo-4-Hydroxyquinoline-3-Carboxylic Acids—a new Group of Potential Antiinflammatory Agents", *Chemistry of Heterocyclic Compounds*, vol. 30 (10), pp. 1211-1213 (1994).
Wright, J.L., et al., "A Neutrophil Elastase Inhibitor Reduces Cigarette Smoke-Induced Remodelling of Lung Vessels", *Eur. Respir. J.*, vol. 22, pp. 77-81 (2003).
Zeiher, B.G., et al., "Neutrophil Elastase and Acute Lung Injury: Prospects for Sivelestat and Other Neutrophil Elastase Inhibitors as Therapeutics", *Crit. Care Med.*, vol. 30 (5), pp. S281-S287 (2002).
Harayama, T., et al., "Hydrolysis Products of Flavins (Isoalloxazines)", *J. Chem. Soc. Perkin Trans. I*, pp. 75-83 (1987).
Beilstein Institute for Organic Chemistry, XP002481053 & KHIM Geterotsikl Soedin, vol. 34 (1), pp. 73-76 (1998).
Europ. Resp. Soc., http://www.newtocopd.com/currentaffairsnews/list751_item17680.aspx; (2008).
STN International, File CAPLUS, CAPLUS accession No. 1995:456529, Document No. 123:198678, Ukrainets, I.V. et al.: "4-Hydroxy-2-Quinolones. 23. N-(2-Thiazolyl) amides of 1-Substituted 4-Hydroxy-2-Oxoquinoline-3-Carboxylic Acids—a New Group of Potential Anti-inflammatory Drugs"; & Khimiya Geterotsiklicheskikh Soedinenii (10), 1397-9 (1994).
STN International, File CAPLUS, CAPLUS accession Nno. 1990:611864, Document No. 113:211864, Otsuka Pharmaceutical Co., Ltd.: "4-Hydroxycarbostyrils as Anti-Inflammatory and Antiallergy Agents", JP, A2, 02152966, 19900612 (1990).
United States Pharmacopeia and National Formulary (USP 35-NF 30). 1st Supp. Rockville, MD: United States Pharmacopeia Convention; 2012: 941, 1005.

SOME 2-PYRAZINONE DERIVATIVES AND THEIR USE AS INHIBITORS OF NEUTROPHILE ELASTASE

CROSS-REFERENCE TO RELATED APPLICATIONS

This application is a US National Stage under 35 U.S.C §371 of International Application No. PCT/SE2008/051263 (filed 5 Nov. 2008) which claims priority under 35 U.S.C. §119(e) to Application No. 60/985,713 filed on 6 Nov. 2007.

FIELD OF THE INVENTION

The present invention relates to 2-pyrazinone derivatives, processes for their preparation, pharmaceutical compositions containing them and their use in therapy.

BACKGROUND OF THE INVENTION

Elastases are possibly the most destructive enzymes in the body, having the ability to degrade virtually all connective tissue components. The uncontrolled proteolytic degradation by elastases has been implicated in a number of pathological conditions. Human neutrophil elastase (hNE), a member of the chymotrypsin superfamily of serine proteases is a 33-KDa enzyme stored in the azurophilic granules of the neutrophils. In neutrophils the concentration of NE exceeds 5 mM and its total cellular amount has been estimated to be up to 3 pg. Upon activation, NE is rapidly released from the granules into is the extracellular space with some portion remaining bound to neutrophil plasma membrane (See Kawabat et al. 2002, Eur. J. Pharmacol. 451, 1-10). The main intracellular physiological function of NE is degradation of foreign organic molecules phagocytosed by neutrophils, whereas the main target for extracellular elastase is elastin (Janoff and Scherer, 1968, J. Exp. Med. 128, 1137-1155). NE is unique, as compared to other proteases (for example, proteinase 3) in that it has the ability to degrade almost all extracellular matrix and key plasma proteins (See Kawabat et al., 2002, Eur. J. Pharmacol. 451, 1-10). It degrades a wide range of extracellular matrix proteins such as elastin, Type 3 and type 4 collagens, laminin, fibronectin, cytokines, etc. (Ohbayashi, H., 2002, Expert Opin. Investig. Drugs, 11, 965-980). NE is a major common mediator of many pathological changes seen in chronic lung disease including epithelial damage (Stockley, R. A. 1994, Am. J. Resp. Crit. Care Med. 150, 109-113).

The destructive role of NE was solidified almost 40 years ago when Laurell and Eriksson reported an association of chronic airflow obstruction and emphysema with deficiency of serum $\alpha_1$-antitrypsin (Laurell and Eriksson, 1963, Scand. J. Clin. Invest. 15, 132-140). Subsequently it was determined that $\alpha_1$-antitrypsin is the most important endogenous inhibitor of human NE. The imbalance between human NE and endogenous antiprotease is believed to cause excess human NE in pulmonary tissues which is considered as a major pathogenic factor in chronic obstructive pulmonary disease (COPD). The excessive human NE shows a prominent destructive profile and actively takes part in destroying the normal pulmonary structures, followed by the irreversible enlargement of the respiratory airspaces, as seen mainly in emphysema. There is an increase in neutrophil recruitment into the lungs which is associated with increased lung elastase burden and emphysema in $\alpha_1$-proteinase inhibitor-deficient mice (Cavarra et al., 1996, Lab. Invest. 75, 273-280). Individuals with higher levels of the NE-$\alpha_1$ protease inhibitor complex in bronchoalveolar lavage fluid show significantly accelerated decline in lung functions compared to those with lower levels (Betsuyaku et al. 2000, Respiration, 67, 261-267). Instillation of human NE via the trachea in rats causes lung haemorrhage, neutrophil accumulation during acute phase and emphysematous changes during chronic phase (Karaki et al., 2002, Am. J. Resp. Crit. Care Med., 166, 496-500). Studies have shown that the acute phase of pulmonary emphysema and pulmonary haemorrhage caused by NE in hamsters can be inhibited by pre-treatment is with inhibitors of NE (Fujie et al., 1999, Inflamm. Res. 48, 160-167).

Neutrophil-predominant airway inflammation and mucus obstruction of the airways are major pathologic features of COPD, including cystic fibrosis and chronic bronchitis. NE impairs mucin production, leading to mucus obstruction of the airways. NE is reported to increase the expression of major respiratory mucin gene, MUC5AC (Fischer, B. M & Voynow, 2002, Am. J. Respir. Cell Biol., 26, 447-452). Aerosol administration of NE to guinea pigs produces extensive epithelial damage within 20 minutes of contact (Suzuki et al., 1996, Am. J. Resp. Crit. Care Med., 153, 1405-1411). Furthermore NE reduces the ciliary beat frequency of human respiratory epithelium in vitro (Smallman et al., 1984, Thorax, 39, 663-667) which is consistent with the reduced mucociliary clearance that is seen in COPD patients (Currie et al., 1984, Thorax, 42, 126-130). The instillation of NE into the airways leads to mucus gland hyperplasia in hamsters (Lucey et al., 1985, Am. Resp. Crit. Care Med., 132, 362-366). A role for NE is also implicated in mucus hypersecretion in asthma. In an allergen sensitised guinea pig acute asthma model an inhibitor of NE prevented goblet cell degranulation and mucus hypersecretion (Nadel et al., 1999, Eur. Resp. J., 13, 190-196).

NE has been also shown to play a role in the pathogenesis of pulmonary fibrosis. NE: $\alpha_1$-protease inhibitor complex is increased in serum of patients with pulmonary fibrosis, which correlates with the clinical parameters in these patients (Yamanouchi et al., 1998, Eur. Resp. J. 11, 120-125). In a murine model of human pulmonary fibrosis, a NE inhibitor reduced bleomycin-induced pulmonary fibrosis (Taooka et al., 1997, Am. J. Resp. Crit. Care Med., 156, 260-265). Furthermore investigators have shown that NE deficient mice are resistant to bleomycin-induced pulmonary fibrosis (Dunsmore et al., 2001, Chest, 120, 35S-36S). Plasma NE level was found to be elevated in patients who progressed to ARDS implicating the importance of NE in early ARDS disease pathogenesis. (Donnelly et al., 1995, Am. J. Res. Crit. Care Med., 151, 428-1433). The antiproteases and NE complexed with antiprotease are increased in lung cancer area (Marchandise et al., 1989, Eur. Resp. J. 2, 623-629). Recent studies have shown that polymorphism in the promoter region of the NE gene are associated with lung cancer development (Taniguchi et al., 2002, Clin. Cancer Res., 8, 1115-1120.

Acute lung injury caused by endotoxin in experimental animals is associated with elevated levels of NE (Kawabata, et al., 1999, Am. J. Resp. Crit. Care, 161, 2013-2018). Acute lung inflammation caused by intratracheal injection of lipopolysaccharide in mice has been shown to elevate the NE activity in bronchoalveolar lavage fluid which is significantly inhibited by a NE inhibitor (Fujie et al., 1999, Eur. J. Pharmacol., 374, 117-125; Yasui, et al., 1995, Eur. Resp. J., 8, 1293-1299). NE also plays an important role in the neutrophil-induced increase of pulmonary microvascular permeability observed in a model of acute lung injury caused by tumour necrosis factor $\alpha$ (TNF$\alpha$) and phorbol myristate acetate (PMA) in isolated perfused rabbit lungs (Miyazaki et al., 1998, Am. J. Respir. Crit. Care Med., 157, 89-94).

A role for NE has also been suggested in monocrotoline-induced pulmonary vascular wall thickening and cardiac hypertrophy (Molteni et al., 1989, Biochemical Pharmacol. 38, 2411-2419). Serine elastase inhibitor reverses the monocrotaline-induced pulmonary hypertension and remodelling in rat pulmonary arteries (Cowan et al., 2000, Nature Medicine, 6, 698-702). Recent studies have shown that serine elastase, that is, NE or vascular elastase are important in cigarette smoke-induced muscularisation of small pulmonary arteries in guinea pigs (Wright et al., 2002, Am. J. Respir. Crit. Care Med., 166, 954-960).

NE plays a key role in experimental cerebral ischemic damage (Shimakura et al., 2000, Brain Research, 858, 55-60), ischemia-reperfusion lung injury (Kishima et al., 1998, Ann. Thorac. Surg. 65, 913-918) and myocardial ischemia in rat heart (Tiefenbacher et al., 1997, Eur. J. Physiol., 433, 563-570). Human NE levels in plasma are significantly increased above normal in inflammatory bowel diseases, for example, Crohn's disease and ulcerative colitis (Adeyemi et al., 1985, Gut, 26, 1306-1311). In addition NE has also been assumed to be involved in the pathogenesis of rheumatoid arthritis (Adeyemi et al., 1986, Rheumatol. Int., 6, 57). The development of collagen induced arthritis in mice is suppressed by a NE inhibitor (Kakimoto et al., 1995, Cellular Immunol. 165, 26-32).

Thus, human NE is known as one of the most destructive serine proteases and has been is implicated in a variety of inflammatory diseases. The important endogenous inhibitor of human NE is $\alpha_1$-antitrypsin. The imbalance between human NE and antiprotease is believed to give rise to an excess of human NE resulting in uncontrolled tissue destruction. The protease/antiprotease balance may be upset by a decreased availability of $\alpha_1$-antitrypsin either through inactivation by oxidants such as cigarette smoke, or as a result of genetic inability to produce sufficient serum levels. Human NE has been implicated in the promotion or exacerbation of a number of diseases such as pulmonary emphysema, pulmonary fibrosis, adult respiratory distress syndrome (ARDS), ischemia reperfusion injury, rheumatoid arthritis and pulmonary hypertension.

We now disclose a group of compounds that are potent inhibitors of human NE and also have advantageous pharmacokinetic and physical properties.

DISCLOSURE OF THE INVENTION

Figure 1:
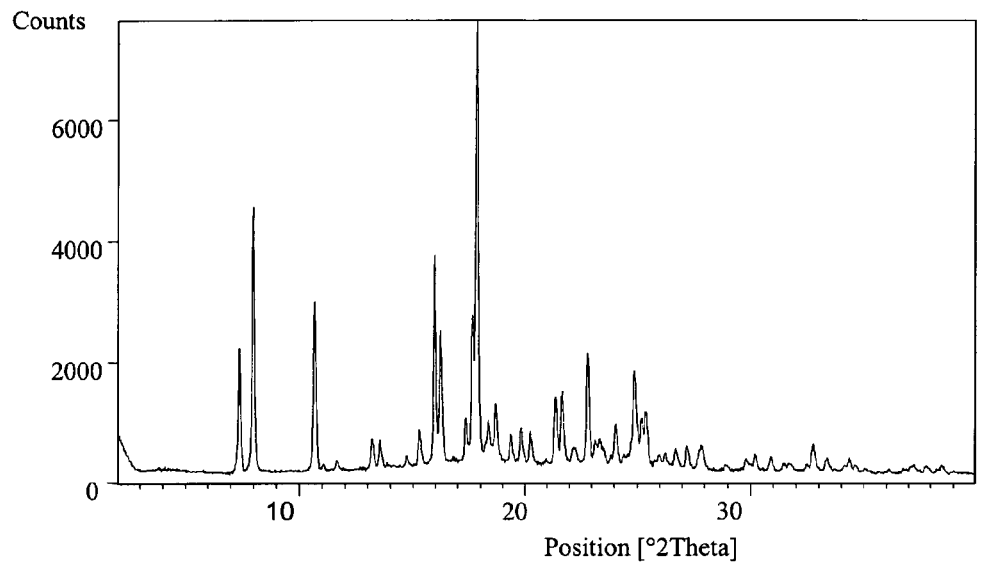
FIG. 1 is an X-ray powder diffraction diagram of 6-[1-(4-cyanophenyl)-1H-pyrazol-5-yl]-5-methyl-3-oxo-4-[3-(trifluoromethyl)phenyl]-3,4-dihydropyrazine-2-carboxamide Form A.

In accordance with the present invention, there is therefore provided a compound selected from:
6-[1-(4-cyanophenyl)-1H-pyrazol-5-yl]-5-methyl-3-oxo-4-[3-(trifluoromethyl)phenyl]-3,4-dihydropyrazine-2-carboxamide;
6-[1-(4-chlorophenyl)-1H-pyrazol-5-yl]-5-methyl-3-oxo-4-[3-(trifluoromethyl)phenyl]-3,4-dihydropyrazine-2-carboxamide;
6-[1-(5-chloropyridin-2-yl)-1H-pyrazol-5-yl]-5-methyl-3-oxo-4-[3-(trifluoromethyl)phenyl]-3,4-dihydropyrazine-2-carboxamide;
6-[1-(4-cyanophenyl)-3-methyl-1H-pyrazol-5-yl]-5-methyl-3-oxo-4-[3-(trifluoromethyl)phenyl]-3,4-dihydropyrazine-2-carboxamide;
4-(3-cyanophenyl)-6-[1-(4-cyanophenyl)-1H-pyrazol-5-yl]-N-cyclopropyl-5-methyl-3-oxo-3,4-dihydropyrazine-2-carboxamide; and
6-(1-(4-cyanophenyl)-4,4-dimethyl-4,5-dihydro-1H-imidazol-2-yl)-5-methyl-3-oxo-4-(3-(trifluoromethyl)phenyl)-3,4-dihydropyrazine-2-carboxamide;
or a pharmaceutically acceptable salt of any one thereof.

In one embodiment, the compound is 6-[1-(4-cyanophenyl)-1H-pyrazol-5-yl]-5-methyl-3-oxo-4-[3-(trifluoromethyl)phenyl]-3,4-dihydropyrazine-2-carboxamide;
or a pharmaceutically acceptable salt thereof.

In one embodiment, the compound is 6-[1-(4-chlorophenyl)-1H-pyrazol-5-yl]-5-methyl-3-oxo-4-[3-(trifluoromethyl)phenyl]-3,4-dihydropyrazine-2-carboxamide;
or a pharmaceutically acceptable salt thereof.

In one embodiment, the compound is 6-[1-(5-chloropyridin-2-yl)-1H-pyrazol-5-yl]-5-methyl-3-oxo-4-[3-(trifluoromethyl)phenyl]-3,4-dihydropyrazine-2-carboxamide;
or a pharmaceutically acceptable salt thereof.

In one embodiment, the compound is 6-[1-(4-cyanophenyl)-3-methyl-1H-pyrazol-5-yl]-5-methyl-3-oxo-4-[3-(trifluoromethyl)phenyl]-3,4-dihydropyrazine-2-carboxamide;
or a pharmaceutically acceptable salt thereof.

In one embodiment, the compound is 4-(3-cyanophenyl)-6-[1-(4-cyanophenyl)-1H-pyrazol-5-yl]-N-cyclopropyl-5-methyl-3-oxo-3,4-dihydropyrazine-2-carboxamide;
or a pharmaceutically acceptable salt thereof.

In one embodiment, the compound is 6-(1-(4-cyanophenyl)-4,4-dimethyl-4,5-dihydro-1H-imidazol-2-yl)-5-methyl-3-oxo-4-(3-(trifluoromethyl)phenyl)-3,4-dihydropyrazine-2-carboxamide;
or a pharmaceutically acceptable salt thereof.

Compound names were generated using the software ACD Labs version 6.00. Corresponding molecular structures are shown in the Examples section.

The present invention further provides a process for the preparation of a compound as listed above or a pharmaceutically acceptable salt thereof.

Specific processes for the preparation of each compound as listed above are disclosed within the Examples section of the present specification. Such processes form an aspect of the present invention.

The necessary starting materials are either commercially available, are known in the literature or may be prepared using known techniques. Specific processes for the preparation of certain key starting materials are disclosed within the Examples section of the present specification and such processes form an aspect of the present invention.

Certain intermediates may be novel. Such novel intermediates form another aspect of the invention.

It will be appreciated by those skilled in the art that in the processes of the present is invention certain functional groups such as hydroxyl or amino groups may need to be protected by protecting groups. Thus, the preparation of the compounds as listed above may involve, at an appropriate stage, the addition and/or removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 3$^{rd}$ edition, T. W. Greene and P. G. M. Wuts, Wiley-Interscience (1999).

The compounds as listed above may be converted to a pharmaceutically acceptable salt thereof, preferably an acid addition salt such as a hydrochloride, hydrobromide, sulphate, phosphate, acetate, fumarate, maleate, tartrate, lactate, citrate, pyruvate, succinate, oxalate, methanesulphonate or p-toluenesulphonate.

It will be understood that where such isomeric forms exist, the invention encompasses the use of all geometric and optical isomers (including atropisomers) of the compounds as listed above and mixtures thereof. The use of tautomers and mixtures thereof also form an aspect of the present invention.

Polymorphism can be characterised as the ability of a particular compound to crystallise in different crystal modifications whilst maintaining the same chemical formula. Polymorphs of a given substance are chemically identical in containing the same atoms bonded to one another in the same way, but differ in their crystal modifications, which can affect one or more physical properties such as dissolution rate, melting point, bulk density, stability, flow properties, etc. As used in the specification with reference to a specific compound, the terms "polymorph", "crystal modification", "crystal form", "crystalline modification" and "(crystalline) Form" are to be understood as synonymous.

In one embodiment, the invention provides a crystalline modification of 6-[1-(4-cyanophenyl)-1H-pyrazol-5-yl]-5-methyl-3-oxo-4-[3-(trifluoromethyl)phenyl]-3,4-dihydropyrazine-2-carboxamide designated Form A and characterised by having an X-ray powder diffraction (XPRD) pattern comprising specific peaks at 8.0, 15.9 and 17.8°2θ and wherein said XPRD pattern is measured using CuK$_\alpha$ radiation.

In another embodiment, the invention provides a crystalline modification of 6-[1-(4-cyanophenyl)-1H-pyrazol-5-yl]-5-methyl-3-oxo-4-[3-(trifluoromethyl)phenyl]-3,4-dihydropyrazine-2-carboxamide designated Form A and characterised by having an X-ray powder diffraction (XPRD) pattern comprising specific peaks at 7.4, 8.0, 10.7, 15.9, 16.2, 17.6, 17.8, 21.6, 22.8 and 24.9°2θ and wherein said XPRD pattern is measured using CuK$_\alpha$ radiation.

In another embodiment, the invention provides a crystalline modification of 6-[1-(4-cyanophenyl)-1H-pyrazol-5-yl]-5-methyl-3-oxo-4-[3-(trifluoromethyl)phenyl]-3,4-dihydropyrazine-2-carboxamide designated Form A and characterised by having an X-ray powder diffraction (XPRD) pattern substantially the same as that shown in FIG. 1 and wherein said XPRD pattern is measured using CuK$_\alpha$ radiation.

In another embodiment, the invention provides a crystalline modification of 6-[1-(4-cyanophenyl)-1H-pyrazol-5-yl]-5-methyl-3-oxo-4-[3-(trifluoromethyl)phenyl]-3,4-dihydropyrazine-2-carboxamide designated Form B and characterised by having an X-ray powder diffraction pattern comprising specific peaks at 18.0, 18.2 and 24.7°2θ.

In another embodiment, the invention provides a crystalline modification of 6-[1-(4-cyanophenyl)-1H-pyrazol-5-yl]-5-methyl-3-oxo-4-[3-(trifluoromethyl)phenyl]-3,4-dihydropyrazine-2-carboxamide designated Form B and characterised by having an X-ray powder diffraction pattern comprising specific peaks at 12.5, 14.3, 14.4, 15.7, 17.5, 18.0, 18.2, 18.8, 22.2 and 24.7°2θ.

Figure 2:
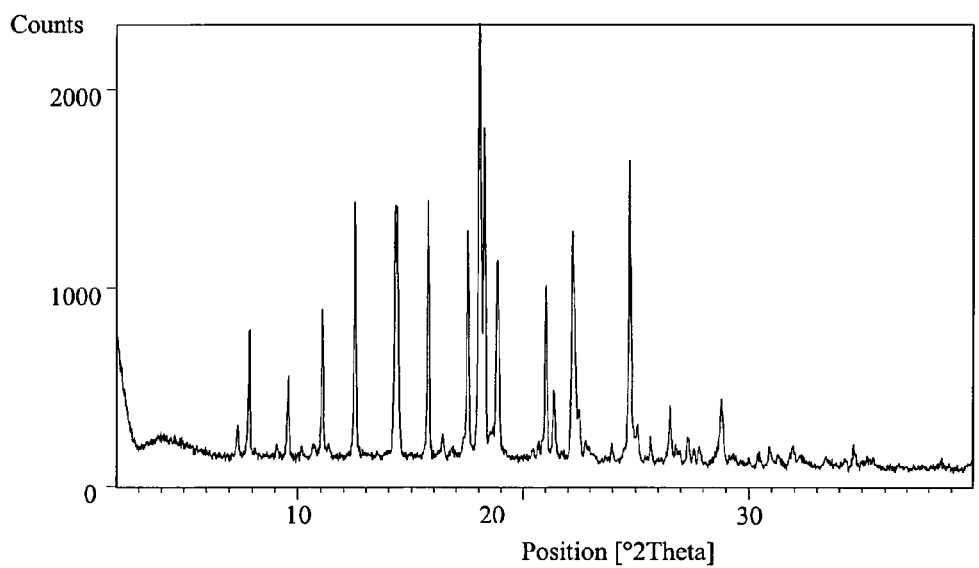
FIG. 2 is an X-ray powder diffraction diagram of 6-[1-(4-cyanophenyl)-1H-pyrazol-5-yl]-5-methyl-3-oxo-4-[3-(trifluoromethyl)phenyl]-3,4-dihydropyrazine-2-carboxamide Form B.

In another embodiment, the invention provides a crystalline modification of 6-[1-(4-cyanophenyl)-1H-pyrazol-5-yl]-5-methyl-3-oxo-4-[3-(trifluoromethyl)phenyl]-3,4-dihydropyrazine-2-carboxamide designated Form B and characterised by having an X-ray powder diffraction pattern substantially the same as that shown in FIG. 2.

In another embodiment, the invention provides a crystalline modification of 6-[1-(4-cyanophenyl)-1H-pyrazol-5-yl]-5-methyl-3-oxo-4-[3-(trifluoromethyl)phenyl]-3,4-dihydropyrazine-2-carboxamide designated Form C and characterised by having an X-ray powder diffraction pattern comprising specific peaks at 7.6, 20.1 and 22.9°2θ.

In another embodiment, the invention provides a crystalline modification of 6-[1-(4-cyanophenyl)-1H-pyrazol-5-yl]-5-methyl-3-oxo-4-[3-(trifluoromethyl)phenyl]-3,4-dihydropyrazine-2-carboxamide designated Form C and characterised by having an X-ray powder diffraction pattern comprising specific peaks at 7.6, 8.6, 10.7, 12.1, 16.6, 17.1, 20.1, 20.2, 22.7 and 22.9°2θ.

Figure 3:
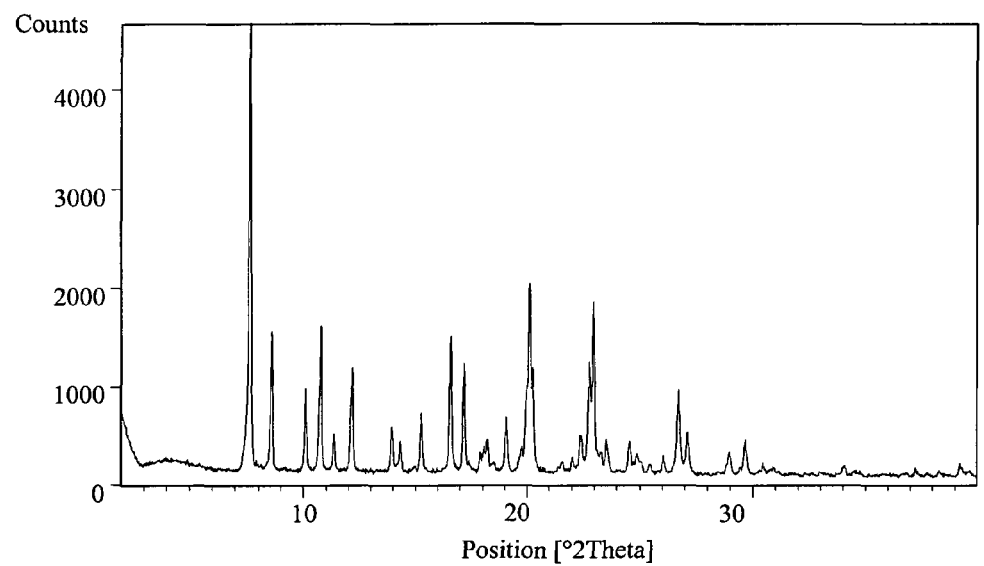
FIG. 3 is an X-ray powder diffraction diagram of 6-[1-(4-cyanophenyl)-1H-pyrazol-5-yl]-5-methyl-3-oxo-4-[3-(trifluoromethyl)phenyl]-3,4-dihydropyrazine-2-carboxamide Form C.

In another embodiment, the invention provides a crystalline modification of 6-[1-(4-cyanophenyl)-1H-pyrazol-5-yl]-5-methyl-3-oxo-4-[3-(trifluoromethyl)phenyl]-3,4-dihydropyrazine-2-carboxamide designated Form C and characterised by having an X-ray powder diffraction pattern substantially the same as that shown in FIG. 3.

In another embodiment, the invention provides a crystalline modification of 6-[1-(4-cyanophenyl)-1H-pyrazol-5-yl]-5-methyl-3-oxo-4-[3-(trifluoromethyl)phenyl]-3,4-dihydropyrazine-2-carboxamide designated Form D and characterised by having an X-ray powder diffraction pattern comprising specific peaks at 7.4, 10.6 and 18.2°2θ.

In another embodiment, the invention provides a crystalline modification of 6-[1-(4-cyanophenyl)-1H-pyrazol-5-yl]-5-methyl-3-oxo-4-[3-(trifluoromethyl)phenyl]-3,4-dihydropyrazine-2-carboxamide designated Form D and characterised by having an X-ray powder diffraction pattern comprising specific peaks at 7.4, 10.6, 17.3, 18.2, 18.5, 21.4, 22.8, 23.1, 24.8 and 24.9°2θ.

Figure 4:
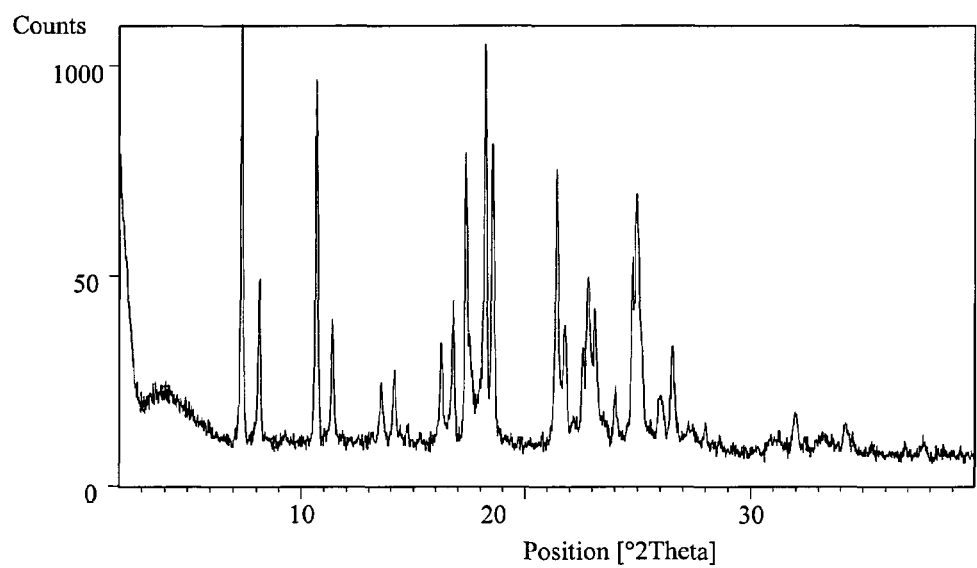
FIG. 4 is an X-ray powder diffraction diagram of 6-[1-(4-cyanophenyl)-1H-pyrazol-5-yl]-5-methyl-3-oxo-4-[3-(trifluoromethyl)phenyl]-3,4-dihydropyrazine-2-carboxamide Form D.

In another embodiment, the invention provides a crystalline modification of 6-[1-(4-cyanophenyl)-1H-pyrazol-5-yl]-5-methyl-3-oxo-4-[3-(trifluoromethyl)phenyl]-3,4-dihydropyrazine-2-carboxamide designated Form D and characterised by having an X-ray powder diffraction pattern substantially the same as that shown in FIG. 4.

In another embodiment, the invention provides a crystalline modification of 6-[1-(4-cyanophenyl)-1H-pyrazol-5-yl]-5-methyl-3-oxo-4-[3-(trifluoromethyl)phenyl]-3,4-dihydropyrazine-2-carboxamide designated Form E and characterised by having an X-ray powder diffraction pattern comprising specific peaks at 7.4, 10.1 and 19.0°2θ.

In another embodiment, the invention provides a crystalline modification of 6-[1-(4-cyanophenyl)-1H-pyrazol-5-yl]-5-methyl-3-oxo-4-[3-(trifluoromethyl)phenyl]-3,4-dihydropyrazine-2-carboxamide designated Form E and characterised by having an X-ray powder diffraction pattern comprising specific peaks at 6.9, 7.4, 10.1, 14.7, 15.0, 15.7, 16.4, 19.0, 19.3 and 22.5°2θ.

Figure 5:
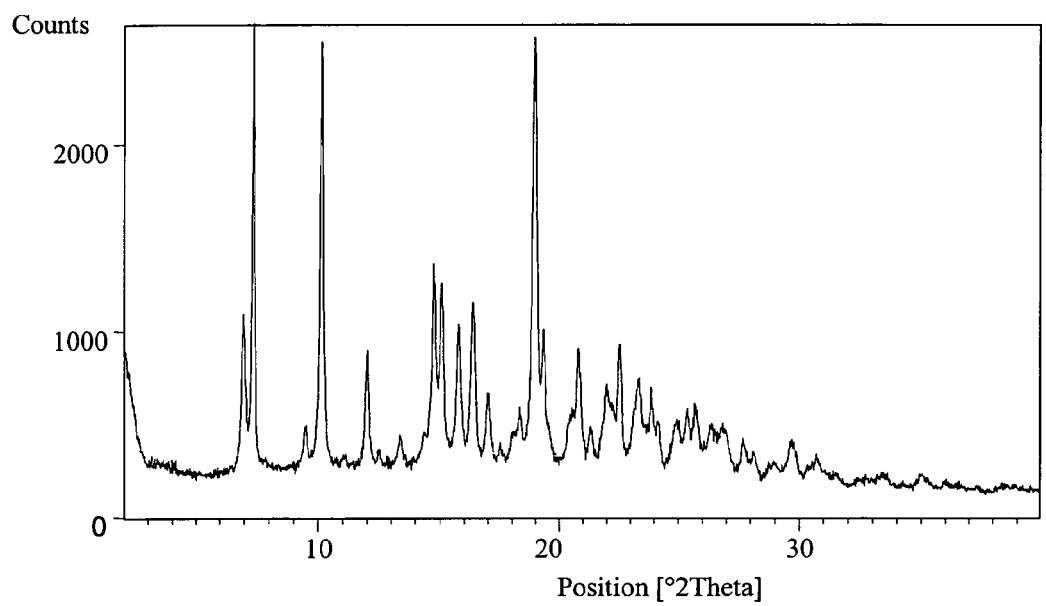
FIG. 5 is an X-ray powder diffraction diagram of 6-[1-(4-cyanophenyl)-1H-pyrazol-5-yl]-5-methyl-3-oxo-4-[3-(trifluoromethyl)phenyl]-3,4-dihydropyrazine-2-carboxamide Form E.

In another embodiment, the invention provides a crystalline modification of 6-[1-(4-cyanophenyl)-1H-pyrazol-5-yl]-5-methyl-3-oxo-4-[3-(trifluoromethyl)phenyl]-3,4-dihydropyrazine-2-carboxamide designated Form E and characterised by having an X-ray powder diffraction pattern substantially the same as that shown in FIG. 5.

It will be understood that the relative intensities of peaks in an X-ray powder diffraction (XPRD) pattern may vary according to the orientation of the sample under test and on the type and setting of the instrument used, so that the intensities in the XPRD traces included herein are to such extent illustrative and are not intended to be used for absolute comparisons.

The crystalline modifications or Forms of the invention are preferably substantially pure, meaning that each crystalline modification or Form of the compound 6-[1-(4-cyanophenyl)-1H-pyrazol-5-yl]-5-methyl-3-oxo-4-[3-(trifluoromethyl)phenyl]-3,4-dihydropyrazine-2-carboxamide includes less than 10%, preferably less than 5%, preferably less than 3%, preferably less than 1% by weight of impurities, including other crystalline modifications or Forms of the compound.

Thus, in one embodiment, the invention provides a substantially pure crystalline modification of 6-[1-(4-cyanophenyl)-1H-pyrazol-5-yl]-5-methyl-3-oxo-4-[3-(trifluoromethyl)phenyl]-3,4-dihydropyrazine-2-carboxamide designated Form A and characterised by having an X-ray powder diffraction (XPRD) pattern comprising specific peaks at 8.0, 15.9 and 17.8°2θ and wherein said XPRD pattern is measured using CuK$_\alpha$ radiation.

In another embodiment, the invention provides a substantially pure crystalline modification of 6-[1-(4-cyanophenyl)-1H-pyrazol-5-yl]-5-methyl-3-oxo-4-[3-(trifluoromethyl)phenyl]-3,4-dihydropyrazine-2-carboxamide designated Form A and characterised by having an X-ray powder diffraction (XPRD) pattern comprising specific peaks at 7.4, 8.0, 10.7, 15.9, 16.2, 17.6, 17.8, 21.6, 22.8 and 24.9°2θ and wherein said XPRD pattern is measured using CuK$_\alpha$, radiation.

In another embodiment, the invention provides a substantially pure crystalline modification of 6-[1-(4-cyanophenyl)-1H-pyrazol-5-yl]-5-methyl-3-oxo-4-[3-(trifluoromethyl)phenyl]-3,4-dihydropyrazine-2-carboxamide designated Form A and characterised by having an X-ray powder diffraction (XPRD) pattern substantially the same as that shown in FIG. 1 and wherein said XPRD pattern is measured using CuK$_\alpha$ radiation.

6-[1-(4-Cyanophenyl)-1H-pyrazol-5-yl]-5-methyl-3-oxo-4-[3-(trifluoromethyl)phenyl]-3,4-dihydropyrazine-2-carboxamide Form A is reproducibly produced when 6-[1-(4-cyanophenyl)-1H-pyrazol-5-yl]-5-methyl-3-oxo-4-[3-(trifluoromethyl)phenyl]-3,4-dihydropyrazine-2-carboxamide is crystallised or recrystallised from N,N-dimethyl acetamide or methyl iso-butylketone at about 50 to 60° C. Form A is obtained as a is crystalline powder that is essentially 100% crystalline as determined by X-ray powder diffraction measurements. Differential scanning calorimetry (DSC) shows that 6-[1-(4-cyanophenyl)-1H-pyrazol-5-yl]-5-methyl-3-oxo-4-[3-(trifluoromethyl)phenyl]-3,4-dihydropyrazine-2-carboxamide Form A is a high melting solid with an onset of melting at 270° C. and a peak at 275° C. 6-[1-(4-Cyanophenyl)-1H-pyrazol-5-yl]-5-methyl-3-oxo-4-[3-(trifluoromethyl)phenyl]-3,4-dihydropyrazine-2-carboxamide Form A is non-hygroscopic, showing a water uptake of <0.2 wt % at 0 to 80% relative humidity (RH) at 25° C.

6-[1-(4-Cyanophenyl)-1H-pyrazol-5-yl]-5-methyl-3-oxo-4-[3-(trifluoromethyl)phenyl]-3,4-dihydropyrazine-2-carboxamide Form B is formed when the compound is slurried in water at ambient conditions. Form B is a high melting solid with an onset of melting at 264° C. and a peak at 267° C. It may then recrystallise to Form A and subsequently melt again with an onset at about 270° C. 6-[1-(4-Cyanophenyl)-1H-pyrazol-5-yl]-5-methyl-3-oxo-4-[3-(trifluoromethyl)phenyl]-3,4-dihydropyrazine-2-carboxamide Form B is non-hygroscopic, showing a water uptake of <0.2 wt % at 0 to 80% RH at 25° C.

6-[1-(4-Cyanophenyl)-1H-pyrazol-5-yl]-5-methyl-3-oxo-4-[3-(trifluoromethyl)phenyl]-3,4-dihydropyrazine-2-carboxamide Form C is formed when the compound is crystallised or recrystallised from methanol at ambient conditions. A melting point for Form C has not been observed since upon heating it transforms into Form A at about 150° C.

6-[1-(4-Cyanophenyl)-1H-pyrazol-5-yl]-5-methyl-3-oxo-4-[3-(trifluoromethyl)phenyl]-3,4-dihydropyrazine-2-carboxamide Form D is formed when the compound is slurried in water at ambient conditions. A melting point for Form D has not been observed since upon heating it transforms into Form A at about 210° C.

6-[1-(4-Cyanophenyl)-1H-pyrazol-5-yl]-5-methyl-3-oxo-4-[3-(trifluoromethyl)phenyl]-3,4-dihydropyrazine-2-carboxamide Form E is formed when the compound is slurried in hydroxypropylmethylcellulose (HPMC)/water, for example, in 0.5% HPMC/water, at is ambient conditions. A melting point for 6-[1-(4-cyanophenyl)-1H-pyrazol-5-yl]-5-methyl-3-oxo-4-[3-(trifluoromethyl)phenyl]-3,4-dihydropyrazine-2-carboxamide Form E has not been observed since upon heating it transforms into Form A at about 220° C.

When any of 6-[1-(4-cyanophenyl)-1H-pyrazol-5-yl]-5-methyl-3-oxo-4-[3-(trifluoromethyl)phenyl]-3,4-dihydropyrazine-2-carboxamide Forms A to E are heated, no solvent loss nor any other thermal event is observed prior to either melting or to solid state transformations such as those outlined above.

Using the procedures disclosed herein, 6-[1-(4-cyanophenyl)-1H-pyrazol-5-yl]-5-methyl-3-oxo-4-[3-(trifluoromethyl)phenyl]-3,4-dihydropyrazine-2-carboxamide Form A can be reproducibly manufactured following small, intermediate or large scale synthesis.

6-[1-(4-Cyanophenyl)-1H-pyrazol-5-yl]-5-methyl-3-oxo-4-[3-(trifluoromethyl)phenyl]-3,4-dihydropyrazine-2-carboxamide Form A has excellent and highly advantageous solid-state properties. It is highly crystalline, non-hygroscopic, and is thermally stable below 260° C., showing neither solvent loss nor any other thermal event prior to melting.

In one aspect, the present invention provides 6-[1-(4-cyanophenyl)-1H-pyrazol-5-yl]-5-methyl-3-oxo-4-[3-(trifluoromethyl)phenyl]-3,4-dihydropyrazine-2-carboxamide Form A.

In a further aspect, the present invention provides processes for the preparation of 6-[1-(4-cyanophenyl)-1H-pyrazol-5-yl]-5-methyl-3-oxo-4-[3-(trifluoromethyl)phenyl]-3,4-dihydropyrazine-2-carboxamide Form A. Thus, in one aspect, the invention provides a process for the preparation of 6-[1-(4-cyanophenyl)-1H-pyrazol-5-yl]-5-methyl-3-oxo-4-[3-(trifluoromethyl)phenyl]-3,4-dihydropyrazine-2-carboxamide Form A that involves crystallisation or recrystallisation from N,N-dimethyl acetamide. In another aspect, the invention provides a process for the preparation of 6-[1-(4-cyanophenyl)-1H-pyrazol-5-yl]-5-methyl-3-oxo-4-[3-(trifluoromethyl)phenyl]-3,4-dihydropyrazine-2-carboxamide Form is A that involves crystallisation or recrystallisation from methyl iso-butylketone.

The compounds as listed above and their pharmaceutically acceptable salts have activity as pharmaceuticals, in particular as modulators of serine proteases such as proteinase 3 and pancreatic elastase and, especially, human neutrophil elastase, and may therefore be beneficial in the treatment or prophylaxis of inflammatory diseases and conditions.

The compounds as listed above and their pharmaceutically acceptable salts can be used in the treatment of diseases of the respiratory tract such as obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus.

The compounds as listed above and their pharmaceutically acceptable salts can also be used in the treatment of diseases of bone and joints such as arthritides associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including is ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies.

The compounds as listed above and their pharmaceutically acceptable salts can also be used in the treatment of pain and connective tissue remodelling of musculoskeletal disorders due to injury [for example, sports injury] or disease: arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritits, scleroderma, mixed connective tissue disorder, spondyloarthropathies or periodontal disease (such as periodontitis).

The compounds as listed above and their pharmaceutically acceptable salts can also be used in the treatment of diseases of skin such as psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions.

The compounds as listed above and their pharmaceutically acceptable salts can also be used in the treatment of diseases of the eye such as blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial.

The compounds as listed above and their pharmaceutically acceptable salts can also be used in the treatment of diseases of the gastrointestinal tract such as glossitis, gingivitis, periodontitis; oesophagitis, including reflux; eosinophilic gastroenteritis, mastocytosis, Crohn's disease, colitis including ulcerative colitis, proctitis, pruritis ani; coeliac disease, irritable bowel syndrome, non-inflammatory diarrhea, and food-related allergies which may have effects remote from the gut (for example, migraine, rhinitis or eczema).

The compounds as listed above and their pharmaceutically acceptable salts can also be used in the treatment of diseases of the cardiovascular system such as atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins.

The compounds as listed above and their pharmaceutically acceptable salts can also be used in oncology such as in the treatment of common cancers including prostate, breast, lung, ovarian, pancreatic, bowel and colon, stomach, skin and brain tumors and malignancies is affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes.

In particular, the compounds as listed above and their pharmaceutically acceptable salts may be used in the treatment of adult respiratory distress syndrome (ARDS), cystic fibrosis, pulmonary emphysema, bronchitis including chronic bronchitis, bronchiectasis, chronic obstructive pulmonary disease (COPD), pulmonary hypertension, asthma including refractive asthma, rhinitis, psoriasis, ischemia-reperfusion injury, rheumatoid arthritis, osteoarthritis, systemic inflammatory response syndrome (SIRS), chronic wound, cancer, atherosclerosis, peptic ulcers, Crohn'disease, ulcerative colitis and gastric mucosal injury.

More particularly, the compounds as listed above and their pharmaceutically acceptable salts may be used in the treatment of chronic obstructive pulmonary disease (COPD), cystic fibrosis, bronchiectasis, asthma and rhinitis.

Even more particularly, the compounds as listed above and their pharmaceutically acceptable salts may be used in the treatment of chronic obstructive pulmonary disease (COPD).

Even more particularly, the compounds as listed above and their pharmaceutically acceptable salts may be used in the treatment of cystic fibrosis.

Even more particularly, the compounds as listed above and their pharmaceutically acceptable salts may be used in the treatment of bronchiectasis.

Thus, the present invention provides a compound as listed above or a pharmaceutically-acceptable salt thereof or a Form thereof as hereinbefore defined for use in therapy.

In a further aspect, the present invention provides 6-[1-(4-cyanophenyl)-1H-pyrazol-5-yl]-5-methyl-3-oxo-4-[3-(trifluoromethyl)phenyl]-3,4-dihydropyrazine-2-carboxamide or a pharmaceutically acceptable salt thereof for use in therapy.

In a further aspect, the present invention provides 6-[1-(4-cyanophenyl)-1H-pyrazol-5-yl]-5-methyl-3-oxo-4-[3-(trifluoromethyl)phenyl]-3,4-dihydropyrazine-2-carboxamide Form A for use in therapy.

In a further aspect, the present invention provides 6-[1-(4-cyanophenyl)-1H-pyrazol-5-yl]-5-methyl-3-oxo-4-[3-(trifluoromethyl)phenyl]-3,4-dihydropyrazine-2-carboxamide Form B for use in therapy.

In a further aspect, the present invention provides the use of a compound as listed above or a pharmaceutically acceptable salt thereof or a Form thereof as hereinbefore defined in the manufacture of a medicament for use in therapy.

In a further aspect, the present invention provides the use of a compound as listed above or a pharmaceutically acceptable salt thereof or a Form thereof as hereinbefore defined in the manufacture of a medicament for the treatment of human diseases or conditions in which modulation of neutrophil elastase activity is beneficial.

In a further aspect, the present invention provides the use of a compound as listed above or a pharmaceutically acceptable salt thereof or a Form thereof as hereinbefore defined in the manufacture of a medicament for use in the treatment of an inflammatory disease or condition.

In a further aspect, the present invention provides the use of 6-[1-(4-cyanophenyl)-1H-pyrazol-5-yl]-5-methyl-3-oxo-4-[3-(trifluoromethyl)phenyl]-3,4-dihydropyrazine-2-carboxamide or a pharmaceutically acceptable salt thereof as hereinbefore defined in the manufacture of a medicament for use in the treatment of an inflammatory disease or condition.

In a further aspect, the present invention provides the use of 6-[1-(4-cyanophenyl)-1H-pyrazol-5-yl]-5-methyl-3-oxo-4-[3-(trifluoromethyl)phenyl]-3,4-dihydropyrazine-2-carboxamide Form A as hereinbefore defined in the manufacture of a medicament for use is in the treatment of an inflammatory disease or condition.

In a further aspect, the present invention provides the use of 6-[1-(4-cyanophenyl)-1H-pyrazol-5-yl]-5-methyl-3-oxo-4-[3-(trifluoromethyl)phenyl]-3,4-dihydropyrazine-2-carboxamide Form B as hereinbefore defined in the manufacture of a medicament for use in the treatment of an inflammatory disease or condition.

In a further aspect, the present invention provides the use of a compound as listed above or a pharmaceutically acceptable salt thereof or a Form thereof as hereinbefore defined in the manufacture of a medicament for use in treating adult respiratory distress syndrome (ARDS), cystic fibrosis, pulmonary emphysema, bronchitis including chronic bronchitis, bronchiectasis, chronic obstructive pulmonary disease (COPD), pulmonary hypertension, asthma including refractive asthma, rhinitis, psoriasis, ischemia-reperfusion injury, rheumatoid arthritis, osteoarthritis, systemic inflammatory response syndrome (SIRS), chronic wound, cancer, atherosclerosis, peptic ulcers, Crohn'disease, ulcerative colitis and gastric mucosal injury.

In a further aspect, the present invention provides the use of a compound as listed above or a pharmaceutically acceptable salt thereof or a Form thereof as hereinbefore defined in the manufacture of a medicament for use in treating chronic obstructive pulmonary disease (COPD).

In a further aspect, the present invention provides the use of 6-[1-(4-cyanophenyl)-1H-pyrazol-5-yl]-5-methyl-3-oxo-4-[3-(trifluoromethyl)phenyl]-3,4-dihydropyrazine-2-carboxamide or a pharmaceutically acceptable salt thereof as hereinbefore defined in the manufacture of a medicament for use in treating chronic obstructive pulmonary disease (COPD).

In a further aspect, the present invention provides the use of 6-[1-(4-cyanophenyl)-1H-pyrazol-5-yl]-5-methyl-3-oxo-4-[3-(trifluoromethyl)phenyl]-3,4-dihydropyrazine-2-carboxamide Form A as hereinbefore defined in the manufacture of a medicament for use is in treating chronic obstructive pulmonary disease (COPD).

In a further aspect, the present invention provides the use of 6-[1-(4-cyanophenyl)-1H-pyrazol-5-yl]-5-methyl-3-oxo-4-[3-(trifluoromethyl)phenyl]-3,4-dihydropyrazine-2-carboxamide Form B as hereinbefore defined in the manufacture of a medicament for use in treating chronic obstructive pulmonary disease (COPD).

In a further aspect, the present invention provides a compound as listed above or a pharmaceutically acceptable salt thereof as hereinbefore defined for the treatment of human diseases or conditions in which modulation of neutrophil elastase activity is beneficial.

In a further aspect, the present invention provides a compound as listed above or a pharmaceutically acceptable salt thereof as hereinbefore defined for the treatment of an inflammatory disease or condition.

In a further aspect, the present invention provides 6-[1-(4-cyanophenyl)-1H-pyrazol-5-yl]-5-methyl-3-oxo-4-[3-(trifluoromethyl)phenyl]-3,4-dihydropyrazine-2-carboxamide or a pharmaceutically acceptable salt thereof as hereinbefore defined for the treatment of an inflammatory disease or condition.

In a further aspect, the present invention provides 6-[1-(4-cyanophenyl)-1H-pyrazol-5-yl]-5-methyl-3-oxo-4-[3-(trifluoromethyl)phenyl]-3,4-dihydropyrazine-2-carboxamide Form A as hereinbefore defined for the treatment of an inflammatory disease or condition.

In a further aspect, the present invention provides 6-[1-(4-cyanophenyl)-1H-pyrazol-5-yl]-5-methyl-3-oxo-4-[3-(trifluoromethyl)phenyl]-3,4-dihydropyrazine-2-carboxamide Form B as hereinbefore defined for the treatment of an inflammatory disease or condition.

In a further aspect, the present invention provides a compound as listed above or a pharmaceutically acceptable salt thereof as hereinbefore defined for the treatment of adult respiratory distress syndrome (ARDS), cystic fibrosis, pulmonary emphysema, bronchitis is including chronic bronchitis, bronchiectasis, chronic obstructive pulmonary disease (COPD), pulmonary hypertension, asthma including refractive asthma, rhinitis, psoriasis, ischemia-reperfusion injury, rheumatoid arthritis, osteoarthritis, systemic inflammatory response syndrome (SIRS), chronic wound, cancer, atherosclerosis, peptic ulcers, Crohn'disease, ulcerative colitis and gastric mucosal injury.

In a further aspect, the present invention provides a compound as listed above or a pharmaceutically acceptable salt thereof as hereinbefore defined for the treatment of chronic obstructive pulmonary disease (COPD).

In a further aspect, the present invention provides 6-[1-(4-cyanophenyl)-1H-pyrazol-5-yl]-5-methyl-3-oxo-4-[3-(trifluoromethyl)phenyl]-3,4-dihydropyrazine-2-carboxamide or a pharmaceutically acceptable salt thereof as hereinbefore defined for the treatment of chronic obstructive pulmonary disease (COPD).

In a further aspect, the present invention provides 6-[1-(4-cyanophenyl)-1H-pyrazol-5-yl]-5-methyl-3-oxo-4-[3-(trifluoromethyl)phenyl]-3,4-dihydropyrazine-2-carboxamide Form A as hereinbefore defined for the treatment of chronic obstructive pulmonary disease (COPD).

In a further aspect, the present invention provides 6-[1-(4-cyanophenyl)-1H-pyrazol-5-yl]-5-methyl-3-oxo-4-[3-(trifluoromethyl)phenyl]-3,4-dihydropyrazine-2-carboxamide Form B as hereinbefore defined for the treatment of chronic obstructive pulmonary disease (COPD).

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the is disease or condition in question. Persons at risk of developing a particular disease or condition generally include those having a family history of the disease or condition, or those who have been identified by genetic testing or screening to be particularly susceptible to developing the disease or condition.

The invention also provides a method of treating, or reducing the risk of, a disease or condition in which inhibition of neutrophil elastase activity is beneficial which comprises administering to a patient in need thereof a therapeutically effective amount of a compound as listed above or a pharmaceutically acceptable salt thereof or a Form thereof as hereinbefore defined.

The invention still further provides a method of treating, or reducing the risk of, an inflammatory disease or condition which comprises administering to a patient in need thereof a therapeutically effective amount of a compound as listed above or a pharmaceutically acceptable salt thereof or a Form thereof as hereinbefore defined.

The invention still further provides a method of treating, or reducing the risk of, an inflammatory disease or condition which comprises administering to a patient in need thereof a therapeutically effective amount of 6-[1-(4-cyanophenyl)-1H-pyrazol-5-yl]-5-methyl-3-oxo-4-[3-(trifluoromethyl) phenyl]-3,4-dihydropyrazine-2-carboxamide or a pharmaceutically acceptable salt thereof as hereinbefore defined.

The invention still further provides a method of treating, or reducing the risk of, an inflammatory disease or condition which comprises administering to a patient in need thereof a therapeutically effective amount of 6-[1-(4-cyanophenyl)-1H-pyrazol-5-yl]-5-methyl-3-oxo-4-[3-(trifluoromethyl) phenyl]-3,4-dihydropyrazine-2-carboxamide Form A as hereinbefore defined.

The invention still further provides a method of treating, or reducing the risk of, an inflammatory disease or condition which comprises administering to a patient in need thereof a therapeutically effective amount of 6-[1-(4-cyanophenyl)-1H-pyrazol-5-yl]-5-methyl-3-oxo-4-[3-(trifluoromethyl) phenyl]-3,4-dihydropyrazine-2-carboxamide Form B is as hereinbefore defined.

The invention still further provides a method of treating, or reducing the risk of, adult respiratory distress syndrome (ARDS), cystic fibrosis, pulmonary emphysema, bronchitis including chronic bronchitis, bronchiectasis, chronic obstructive pulmonary disease (COPD), pulmonary hypertension, asthma including refractive asthma, rhinitis, psoriasis, ischemia-reperfusion injury, rheumatoid arthritis, osteoarthritis, systemic inflammatory response syndrome (SIRS), chronic wound, cancer, atherosclerosis, peptic ulcers, Crohn'disease, ulcerative colitis and gastric mucosal injury which comprises administering to a patient in need thereof a therapeutically effective amount of a compound as listed above or a pharmaceutically acceptable salt thereof or a Form thereof as hereinbefore defined.

The invention still further provides a method of treating, or reducing the risk of, chronic obstructive pulmonary disease (COPD) which comprises administering to a patient in need thereof a therapeutically effective amount of a compound as listed above or a pharmaceutically acceptable salt thereof or a Form thereof as hereinbefore defined.

The invention still further provides a method of treating, or reducing the risk of, chronic obstructive pulmonary disease (COPD) which comprises administering to a patient in need thereof a therapeutically effective amount of 6-[1-(4-cyanophenyl)-1H-pyrazol-5-yl]-5-methyl-3-oxo-4-[3-(trifluoromethyl)phenyl]-3,4-dihydropyrazine-2-carboxamide or a pharmaceutically acceptable salt thereof as hereinbefore defined.

The invention still further provides a method of treating, or reducing the risk of, chronic obstructive pulmonary disease (COPD) which comprises administering to a patient in need thereof a therapeutically effective amount of 6-[1-(4-cyanophenyl)-1H-pyrazol-5-yl]-5-methyl-3-oxo-4-[3-(trifluoromethyl)phenyl]-3,4-dihydropyrazine-2-carboxamide Form A as hereinbefore defined.

The invention still further provides a method of treating, or reducing the risk of, chronic obstructive pulmonary disease (COPD) which comprises administering to a patient in need is thereof a therapeutically effective amount of 6-[1-(4-cyanophenyl)-1H-pyrazol-5-yl]-5-methyl-3-oxo-4-[3-(trifluoromethyl)phenyl]-3,4-dihydropyrazine-2-carboxamide Form B as hereinbefore defined.

For the above-mentioned therapeutic uses the dosage administered will, of course, vary with the compound employed, the mode of administration, the treatment desired and the disorder indicated. The daily dosage of the compound of the invention may be in the range from 0.05 mg/kg to 100 mg/kg.

The compounds as listed above or a pharmaceutically acceptable salts thereof or a Form thereof may be used on their own but will generally be administered in the form of a pharmaceutical composition in which the compound/salt/Form (active ingredient) is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound as listed above or a pharmaceutically acceptable salt thereof or a Form thereof as hereinbefore defined, in association with a pharmaceutically acceptable adjuvant, diluent or carrier.

In a further aspect, the present invention provides a pharmaceutical composition comprising 6-[1-(4-cyanophenyl)-1H-pyrazol-5-yl]-5-methyl-3-oxo-4-[3-(trifluoromethyl)phenyl]-3,4-dihydropyrazine-2-carboxamide.

In a further aspect, the present invention provides a pharmaceutical composition comprising 6-[1-(4-cyanophenyl)-1H-pyrazol-5-yl]-5-methyl-3-oxo-4-[3-(trifluoromethyl)phenyl]-3,4-dihydropyrazine-2-carboxamide Form A.

The invention further provides a process for the preparation of a pharmaceutical composition of the invention which comprises mixing a compound as listed above or a pharmaceutically acceptable salt thereof or a Form thereof as hereinbefore defined with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane (HFA) aerosols and dry powder formulations, for example, formulations in the inhaler device known as the Turbuhaler®; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

Dry powder formulations and pressurized HFA aerosols of the compounds of the invention may be administered by oral or nasal inhalation. For inhalation, the compound is desirably finely divided. The finely divided compound preferably has a mass median diameter of less than 10 μm, and may be suspended in a propellant mixture with the assistance of a dispersant, such as a $C_8$-$C_{20}$ fatty acid or salt thereof, (for example, oleic acid), a bile salt, a phospholipid, an alkyl saccharide, a perfluorinated or polyethoxylated surfactant, or other pharmaceutically acceptable dispersant.

The compounds of the invention may also be administered by means of a dry powder inhaler. The inhaler may be a single or a multi dose inhaler, and may be a breath actuated dry powder inhaler.

One possibility is to mix the finely divided compound of the invention with a carrier substance, for example, a mono-, di- or polysaccharide, a sugar alcohol, or another polyol. Suitable carriers are sugars, for example, lactose, glucose, raffinose, melezitose, lactitol, maltitol, trehalose, sucrose, mannitol; and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, for example, that known as the Turbuhaler® in which a dosing unit meters the desired dose which is then inhaled by the patient. With this system the active ingredient, with or without a carrier substance, is delivered to the patient.

For oral administration the compound of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compound of the invention may be admixed with, for example, a vegetable oil or polyethylene glycol. Hard gelatine capsules may contain granules of the compound using either the above-mentioned excipients for tablets. Also liquid or semisolid formulations of the compound of the invention may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, saccharine and/or is carboxymethylcellulose as a thickening agent or other excipients known to those skilled in art.

The compounds of the invention may also be administered in conjunction with other compounds used for the treatment of the above conditions.

Thus, the invention further relates to combination therapies wherein a compound of the invention, or a pharmaceutically acceptable salt thereof, or a Form thereof, or a pharmaceutical composition or formulation comprising a compound of the invention, is administered concurrently or sequentially or as a combined preparation with another therapeutic agent or agents, for the treatment of one or more of the conditions listed. In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with agents listed below.

Non-steroidal anti-inflammatory agents (hereinafter NSAIDs) including non-selective cyclo-oxygenase COX-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumaracoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate; leflunomide; hydroxychloroquine; d-penicillamine; auranofin or other parenteral or oral gold preparations; analgesics; diacerein; intra-articular therapies such as hyaluronic acid derivatives; and nutritional supplements such as glucosamine.

The present invention still further relates to the combination of a compound of the invention, or a pharmaceutically acceptable salt thereof, or a Form thereof, together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 23, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

In addition the invention relates to a combination of a compound of the invention, or a pharmaceutically acceptable salt thereof, or a Form thereof, with a monoclonal antibody targeting B-Lymphocytes (such as CD20 (rituximab), MRA-aIL16R and T-Lymphocytes, CTLA4-Ig, HuMax Il-15).

The present invention still further relates to the combination of a compound of the invention, or a pharmaceutically acceptable salt thereof, or a Form thereof, with a modulator of chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family.

The present invention further relates to the combination of a compound of the invention, or a pharmaceutically acceptable salt thereof, or a Form thereof, with an inhibitor of matrix metalloprotease (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline. The present invention still further relates to the combination of a compound of the invention, or a pharmaceutically acceptable salt thereof, or a Form thereof, and a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; a N-(5-substituted)-thiophene-2-alkylsulfonamide; 2,6-di-tert-butylphenolhydrazones; a methoxytetrahydropyrans such as Zeneca ZD-2138; the compound SB-210661; a pyridinyl-substituted 2-cyanonaphthalene compound such as L-739,010; a 2-cyanoquinoline compound such as L-746, 530; or an indole or quinoline compound such as MK-591, MK-886, and BAY x 1005.

The present invention further relates to the combination of a compound of the invention, or a pharmaceutically acceptable salt thereof, or a Form thereof, and a receptor antagonist for is leukotrienes (LT) B4, LTC4, LTD4, and LTE4. selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195. The present invention still further relates to the combination of a compound of the invention, or a pharmaceutically acceptable salt thereof, or a Form thereof, and a phosphodiesterase (PDE) inhibitor such as a methylxanthanine including theophylline and aminophylline; a selective PDE isoenzyme inhibitor including a PDE4 inhibitor an inhibitor of the isoform PDE4D, or an inhibitor of PDE5.

The present invention further relates to the combination of a compound of the invention, or a pharmaceutically acceptable salt thereof, or a Form thereof, and a histamine type 1 receptor antagonist such as cetirizine, loratadine, desloratadine, fexofenadine, acrivastine, terfenadine, astemizole, azelastine, levocabastine, chlorpheniramine, promethazine, cyclizine, or mizolastine; applied orally, topically or parenterally.

The present invention still further relates to the combination of a compound of the invention, or a pharmaceutically acceptable salt thereof, or a Form thereof, and a proton pump inhibitor (such as omeprazole) or a gastroprotective histamine type 2 receptor antagonist.

The present invention further relates to the combination of a compound of the invention, or a pharmaceutically acceptable salt thereof, or a Form thereof, and an antagonist of the histamine type 4 receptor.

The present invention still further relates to the combination of a compound of the invention, or a pharmaceutically acceptable salt thereof, or a Form thereof, and an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride or ethylnorepinephrine hydrochloride.

The present invention further relates to the combination of a compound of the invention, or a pharmaceutically acceptable salt thereof, or a Form thereof, and an anticholinergic agents is including muscarinic receptor (M1, M2, and M3) antagonist such as atropine, hyoscine, glycopyrrrolate, ipratropium bromide, tiotropium bromide, oxitropium bromide, pirenzepine or telenzepine.

The present invention still further relates to the combination of a compound of the invention, or a pharmaceutically acceptable salt thereof, or a Form thereof, and a beta-adrenoceptor agonist (including beta receptor subtypes 1-4) such as isoprenaline, salbutamol, formoterol, salmeterol, terbutaline, orciprenaline, bitolterol mesylate, or pirbuterol, or a chiral enantiomer thereof.

The present invention further relates to the combination of a compound of the invention, or a pharmaceutically acceptable salt thereof, or a Form thereof, and a chromone, such as sodium cromoglycate or nedocromil sodium.

The present invention still further relates to the combination of a compound of the invention, or a pharmaceutically acceptable salt thereof, or a Form thereof, with a glucocorticoid, such as flunisolide, triamcinolone acetonide, beclomethasone dipropionate, budesonide, fluticasone propionate, ciclesonide or mometasone furoate.

The present invention further relates to the combination of a compound of the invention, or a pharmaceutically acceptable salt thereof, or a Form thereof, with an agent that modulates a nuclear hormone receptor such as PPARs.

The present invention still further relates to the combination of a compound of the invention, or a pharmaceutically acceptable salt thereof, or a Form thereof, together with an immunoglobulin (Ig) or Ig preparation or an antagonist or antibody modulating Ig function such as anti-IgE (for example omalizumab).

The present invention further relates to the combination of a compound of the invention, or a pharmaceutically acceptable salt thereof, or a Form thereof, and another systemic or topically-applied anti-inflammatory agent, such as thalidomide or a derivative thereof, a retinoid, dithranol or calcipotriol.

The present invention still further relates to the combination of a compound of the invention, or a pharmaceutically acceptable salt thereof, or a Form thereof, and combinations of aminosalicylates and sulfapyridine such as sulfasalazine, mesalazine, balsalazide, and olsalazine; and immunomodulatory agents such as the thiopurines, and corticosteroids such as budesonide.

The present invention further relates to the combination of a compound of the invention, or a pharmaceutically acceptable salt thereof, or a Form thereof, together with an antibacterial agent such as a penicillin derivative, a tetracycline, a macrolide, a beta-lactam, a fluoroquinolone, metronidazole, an inhaled aminoglycoside; an antiviral agent including acyclovir, famciclovir, valaciclovir, ganciclovir, cidofovir, amantadine, rimantadine, ribavirin, zanamavir and oseltamavir; a protease inhibitor such as indinavir, nelfinavir, ritonavir, and saquinavir; a nucleoside reverse transcriptase inhibitor such as didanosine, lamivudine, stavudine, zalcitabine or zidovudine; or a non-nucleoside reverse transcriptase inhibitor such as nevirapine or efavirenz.

The present invention still further relates to the combination of a compound of the invention, or a pharmaceutically acceptable salt thereof, or a Form thereof, and a cardiovascular agent such as a calcium channel blocker, a beta-adrenoceptor blocker, an angiotensin-converting enzyme (ACE) inhibitor, an angiotensin-2 receptor antagonist; a lipid lowering agent such as a statin or a fibrate; a modulator of blood cell morphology such as pentoxyfylline; thrombolytic, or an anticoagulant such as a platelet aggregation inhibitor.

The present invention further relates to the combination of a compound of the invention, or a pharmaceutically acceptable salt thereof, or a Form thereof, and a CNS agent such as an antidepressant (such as sertraline), an anti-Parkinsonian drug (such as deprenyl, L-dopa, ropinirole, pramipexole, a MAOB inhibitor such as selegine and rasagiline, a comP inhibitor such as tasmar, an A-2 inhibitor, a dopamine reuptake inhibitor, an NMDA antagonist, a nicotine agonist, a dopamine agonist or an inhibitor of neuronal nitric oxide synthase), or an anti-Alzheimer's drug such as donepezil, rivastigmine, tacrine, a COX-2 inhibitor, propentofylline or metrifonate.

The present invention still further relates to the combination of a compound of the invention, or a pharmaceutically acceptable salt thereof, or a Form thereof, and an agent for the treatment of acute or chronic pain, such as a centrally or peripherally-acting analgesic (for example an opioid or derivative thereof), carbamazepine, phenyloin, sodium valproate, amitryptyline or other anti-depressant agent-s, paracetamol, or a non-steroidal anti-inflammatory agent.

The present invention further relates to the combination of a compound of the invention, or a pharmaceutically acceptable salt thereof, or a Form thereof, together with a parenterally or topically-applied (including inhaled) local anaesthetic agent such as lignocaine or a is derivative thereof.

A compound of the present invention, or a pharmaceutically acceptable salt thereof, or a Form thereof, can also be used in combination with an anti-osteoporosis agent including a hormonal agent such as raloxifene, or a biphosphonate such as alendronate.

The present invention still further relates to the combination of a compound of the invention, or a pharmaceutically acceptable salt thereof, or a Form thereof, together with a: (i) tryptase inhibitor; (ii) platelet activating factor (PAF) antagonist; (iii) interleukin converting enzyme (ICE) inhibitor; (iv) IMPDH inhibitor; (v) adhesion molecule inhibitors including VLA-4 antagonist; (vi) cathepsin; (vii) kinase inhibitor such as an inhibitor of tyrosine kinase (such as Btk, Itk, Jak3 or MAP, for example Gefitinib or Imatinib mesylate), a serine/threonine kinase (such as an inhibitor of a MAP kinase such as p38, JNK, protein kinase A, B or C, or IKK), or a kinase involved in cell cycle regulation (such as a cylin dependent kinase); (viii) glucose-6 phosphate dehydrogenase inhibitor; (ix) kinin-B.sub 1.- or B.sub2.-receptor antagonist; (x) anti-gout agent, for example colchicine; (xi) xanthine oxidase inhibitor, for example allopurinol; (xii) uricosuric agent, for example probenecid, sulfinpyrazone or benzbromarone; (xiii) growth hormone secretagogue; (xiv) transforming growth factor (TGFβ); (xv) platelet-derived growth factor (PDGF); (xvi) fibroblast growth factor for example basic fibroblast growth factor (bFGF); (xvii) granulocyte macrophage colony stimulating factor (GM-CSF); (xviii) capsaicin cream; (xix) tachykinin NK.sub1. or NK.sub3. receptor antagonist such as NKP-608C, SB-233412 (talnetant) or D-4418; (xx) elastase inhibitor such as UT-77 or ZD-0892; (xxi) TNF-alpha converting enzyme inhibitor (TACE); (xxii) induced nitric oxide synthase (iNOS) inhibitor; (xxiii) chemoattractant receptor-homologous molecule expressed on TH2 cells, (such as a CRTH2 antagonist); (xxiv) inhibitor of P38; (xxv) agent modulating the function of Toll-like receptors (TLR), (xxvi) agent modulating the activity of purinergic receptors such as P2X7; or (xxvii) inhibitor of transcription factor activation such as NFkB, API, or STATS.

A compound of the invention, or a pharmaceutically acceptable salt thereof, or a Form thereof, can also be used in combination with an existing therapeutic agent for the treatment of cancer, for example suitable agents include:

(i) an antiproliferative/antineoplastic drug or a combination thereof, as used in medical oncology, such as an alkylating agent (for example cis-platin, carboplatin, is cyclophosphamide, nitrogen mustard, melphalan, chlorambucil, busulphan or a nitrosourea); an antimetabolite (for example an antifolate such as a fluoropyrimidine like 5-fluorouracil or tegafur, raltitrexed, methotrexate, cytosine arabinoside, hydroxyurea, gemcitabine or paclitaxel); an antitumour antibiotic (for example an anthracycline such as adriamycin, bleomycin, doxorubicin, daunomycin, epirubicin, idarubicin, mitomycin-C, dactinomycin or mithramycin); an antimitotic agent (for example a vinca alkaloid such as vincristine, vinblastine, vindesine or vinorelbine, or a taxoid such as taxol or taxotere); or a topoisomerase inhibitor (for example an epipodophyllotoxin such as etoposide, teniposide, amsacrine, topotecan or a camptothecin);

(ii) a cytostatic agent such as an antioestrogen (for example tamoxifen, toremifene, raloxifene, droloxifene or iodoxyfene), an oestrogen receptor down regulator (for example fulvestrant), an antiandrogen (for example bicalutamide, flutamide, nilutamide or cyproterone acetate), a LHRH antagonist or LHRH agonist (for example goserelin, leuprorelin or buserelin), a progestogen (for example megestrol acetate), an aromatase inhibitor (for example as anastrozole, letrozole, vorazole or exemestane) or an inhibitor of 5α-reductase such as finasteride;

(iii) an agent which inhibits cancer cell invasion (for example a metalloproteinase inhibitor like marimastat or an inhibitor of urokinase plasminogen activator receptor function);

(iv) an inhibitor of growth factor function, for example: a growth factor antibody (for example the anti-erbb2 antibody trastuzumab, or the anti-erbb1 antibody cetuximab [C225]), a farnesyl transferase inhibitor, a tyrosine kinase inhibitor or a serine/threonine kinase inhibitor, an inhibitor of the epidermal growth factor family (for example an EGFR family tyrosine kinase inhibitor such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) or 6-acrylamido-N-(3-chloro-4-fluorophenyl)-7-(3-morpholinopropoxy)quinazolin-4-amine (CI 1033)), an inhibitor of the platelet-derived growth factor family, or an inhibitor of the hepatocyte growth factor family;

(v) an antiangiogenic agent such as one which inhibits the effects of vascular endothelial growth factor (for example the anti-vascular endothelial cell growth factor antibody bevacizumab, a compound disclosed in WO 97/22596, WO 97/30035, WO 97/32856 or WO 98/13354), or a compound that works by another mechanism (for example linomide, an inhibitor of integrin αvβ3 function or an angiostatin);

(vi) a vascular damaging agent such as combretastatin A4, or a compound disclosed in WO 99/02166, WO 00/40529, WO 00/41669, WO 01/92224, WO 02/04434 or WO 02/08213;

(vii) an agent used in antisense therapy, for example one directed to one of the targets listed above, such as ISIS 2503, an anti-ras antisense;

(viii) an agent used in a gene therapy approach, for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; or (ix) an agent used in an immunotherapeutic approach, for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies. In particular the compounds of the invention may be administered in conjunction with a second active ingredient which is selected from:

a) a PDE4 inhibitor including an inhibitor of the isoform PDE4D;
    b) a β-adrenoceptor agonist such as metaproterenol, isoproterenol, isoprenaline, albuterol, salbutamol, formoterol, salmeterol, terbutaline, orciprenaline, bitolterol mesylate, pirbuterol or indacaterol;
    c) a muscarinic receptor antagonist (for example a M1, M2 or M3 antagonist, such as a selective M3 antagonist) such as ipratropium bromide, tiotropium bromide, oxitropium bromide, pirenzepine or telenzepine;
    d) a modulator of chemokine receptor function (such as a CCR1 or CCR8 receptor antagonist);
    e) an inhibitor of kinase function;
    f) a non-steroidal glucocorticoid receptor agonist;
    g) a steroidal glucocorticoid receptor agonist; and
    h) a protease inhibitor (such as a MMP12 or MMP9 inhibitor);

The present invention will now be further explained by reference to the following illustrative examples.

General Methods

X-Ray Powder Diffraction (XPRD)

X-Ray Powder Diffraction (XRPD) patterns were collected on a PANalytical X'Pert PRO MPD theta-theta system using nickel-filtered CuK-radiation (1.5418 Å, 45 kV, 40 mA) and an X'Celerator detector. A programmable divergence slit and a programmable anti-scatter slit giving an irradiated length of 10 mm were used. Diffraction patterns were collected between 2 and 40°2θ in a continuous scan mode. The scan speed was 4°/min, with an increment of 0.016°. The measurements were performed at ambient conditions.

Thin flat samples were prepared on flat silicon zero background plates using a Teflon bar. The plates were mounted in sample holders and rotated in a horizontal position during measurement.

XRPD patterns at elevated temperatures were collected using a Anton Paar TTK450 temperature chamber mounted on the instrument described above. A programmable divergence slit and a programmable anti-scatter slit giving an irradiated length of 10 mm were used. Diffraction patterns were collected between 2 and 40°2θ in a continuous scan mode. The scan speed was 6°/min, with an increment of 0.016°. In a standard experiment, the sample temperature was increased in steps of 10° C., and XRPD patterns were collected as soon as the targeted temperatures had been reached. In this manner, a series of XRPD patterns were collected up to the final melting point, for each test sample.

The person skilled in the art of X-ray powder diffraction will realise that the relative intensity of peaks can be affected by, for example, grains above approximately 30 micrometer in size and non-unitary aspect ratios which may affect analysis of samples. Furthermore, it should be understood that intensities may fluctuate depending on experimental conditions and sample preparation such as preferred orientation of the is particles in the sample. The use of automatic or fixed divergence slits will also influence the relative intensity calculations. A person skilled in the art can handle such effects when comparing diffraction patterns.

The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values.

Calorimetry (DSC)

Using standard methods, for example those described in Höhne, G. W. H. et al (1996), Differential Scanning Calorimetry, Springer, Berlin, the calorimetric response of a test sample to increasing temperature was investigated using a TA Instruments Q2000 Modulated Temperature Differential Scanning Calorimeter (MTDSC). Measurements were performed between 15 and 300° C. using a modulation of ±0.50° C. in intervals of 40 seconds and a ramp rate of 5° C. per minute. Approximately 1 to 5 mg of test sample was placed in aluminium cups with lids (no crimping) under a nitrogen atmosphere.

It is well known that the DSC onset and peak temperatures may vary according to the purity of the sample and instrumental parameters, especially the temperature scan rate. A person skilled in the art can use routine optimization/calibration to set up instrumental parameters for a differential scanning calorimeter so that data comparable to the data presented here can be collected.

Gravimetric Analysis (TGA)

The gravimetric response of test samples to increasing temperatures was investigated using a Q500 Thermal Gravimetric Analyser (TGA) (TA Instruments). The samples were heated in a flow of nitrogen gas with a heating rate of 10° C./min.

Approximately 1 to 3 mg of the test sample was placed in the cup and heated to approximately 300° C.

Humidity Interaction is The gravimetric responses of test samples to changes in humidity were investigated using a TGA 5000 (TA Instruments) Gravimetrical Vapour Sorption (GVS). The relative humidity (RH) was raised in steps of 5% to 90% RH and lowered back to 0% RH in two cycles. Each level of RH was held until the equilibrium condition (sample weight change<0.01 wt % per 10 minutes) was reached. Measurements were normally made at 25° C. Approximately 5 mg of the test sample was placed in the cup and evaluated. The hygroscopicity was calculated as the relative change in weight of the sample between the two conditions 0% RH and 80% RH during the second cycle.

$^1$H NMR and $^{13}$C NMR spectra were recorded on a Varian Inova 400 MHz or a Varian Mercury-VX 300 MHz instrument. The central peaks of chloroform-$d_4$ ($\delta_H$ 7.27 ppm), dimethylsulfoxide-$d_6$ ($\delta_H$ 2.50 ppm), acetonitrile-$d_3$ ($\delta_H$ 1.95 ppm) or methanol-$d_4$ ($\delta_H$ 3.31 ppm) were used as internal references. Column chromatography was carried out using silica gel (0.040-0.063 mm, Merck). Unless stated otherwise, starting materials were commercially available. All solvents and commercial reagents were of laboratory grade and were used as received.

The following method was used for LC/MS analysis:

Instrument Agilent 1100; Column Waters Symmetry 2.1×30 mm; Mass APCI; Flow rate 0.7 ml/min; Wavelength 254 nm; Solvent A: water+0.1% TFA; Solvent B: acetonitrile+0.1% TFA; Gradient 15-95%/B 8 min, 95% B 1 min.

Analytical chromatography was run on a Symmetry $C_{18}$-column, 2.1×30 mm with 3.5 μm particle size, with acetonitrile/water/0.1% trifluoroacetic acid as mobile phase in a gradient from 5% to 95% acetonitrile over 8 minutes at a flow of 0.7 ml/min.

The abbreviations or terms used in the examples have the following meanings:

| | |
|---|---|
| THF: | Tetrahydrofuran |
| DCM: | Dichloromethane |
| TFA: | Trifluoroacetic acid |
| DMF: | N,N-Dimethylformamide |
| EtOAc: | Ethyl acetate |
| DMSO: | Dimethyl sulphoxide |
| MTBE: | tert-Butyl methyl ether |
| SM: | Starting material |
| RT: | Room temperature |
| Eq: | Equivalent |

Example 1

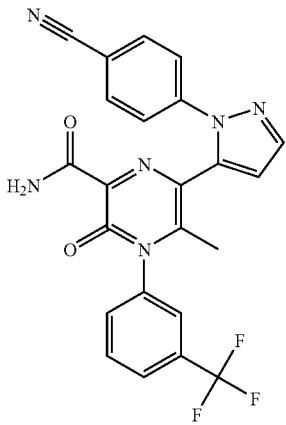

6-[1-(4-Cyanophenyl)-1H-pyrazol-5-yl]-5-methyl-3-oxo-4-[3-(trifluoromethyl)phenyl]-3,4-dihydropyrazine-2-carboxamide

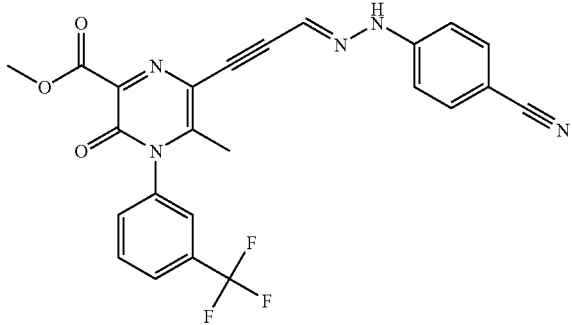 [SMILES: COC(=O)c1nc(C#C/C=N/Nc2ccc(C#N)cc2)c(C)n(-c2cccc(C(F)(F)F)c2)c1=O]

In a 100 mL round-bottomed flask, methyl 6-(3,3-diethoxyprop-1-ynyl)-5-methyl-3-oxo-4-(3-(trifluoromethyl)phenyl)-3,4-dihydropyrazine-2-carboxylate (SM2, 1.136 g, 2.59 mmol) and 4-hydrazinylbenzonitrile hydrochloride (0.508 g, 3.00 mmol) were stirred in methanol (25 mL) and water (2.5 ml) under air at 65° C. After 1 h, the mixture was allowed to cool to 45° C., water (50 ml) was added and the mixture then cooled to RT. After stirring for 30 minutes, the solid was filtered off, washed with water (100 ml) and then air dried to give methyl 6-(3-(2-(4-cyanophenyl)hydrazono)prop-1-ynyl)-5-methyl-3-oxo-4-(3-(trifluoromethyl)phenyl)-3,4-dihydropyrazine-2-carboxylate (1.18 g, 95%) as a yellow solid.

$^1$H NMR (300 MHz, DMSO-$d_6$) δ 2.21 (s, 3H), 3.83 (s, 3H), 7.01 (s, 1H), 7.32 (d, 2H), 7.66 (d, 2H), 7.78-8.00 (m, 4H), 10.55 (s, 1H).

APCI-MS $^m$/z: [MH$^+$=480] the LC showed 2 peaks with M+H=480—cis and trans isomers.

Methyl 6-(3-(2-(4-cyanophenyl)hydrazono)prop-1-ynyl)-5-methyl-3-oxo-4-(3-(trifluoromethyl)phenyl)-3,4-dihydropyrazine-2-carboxylate (1.713 g, 3.57 mmol) was mixed with 7.0M ammonia in methanol (35 mL, 1624.56 mmol), divided into two portions and each portion was separately run in a 20 ml microwave vial in a Biotage Initiator at 120° C. for 20 minutes. A 10 bar pressure was observed during the reaction. The two reaction mixtures were combined and evaporated to give a dark brown residue (1.756 g) which was dissolved in a small volume of MeCN, loaded onto a dry silica column 2.5 (1)×7 (diam) cm and eluted with 0:10 to 4:6 MeCN:t-butyl methyl ether under suction. Pure fractions were evaporated to give a brown material (1.29 g) that was dissolved in warm absolute ethanol (13 ml), stirred at 50° C. for half an hour, then overnight at RT. The solid was filtered off and dried to give 6-[1-(4-cyanophenyl)-1H-pyrazol-5-yl]-5-methyl-3-oxo-4-[3-(trifluoromethyl)phenyl]-3,4-dihydropyrazine-2-carboxamide (0.9699 g, 58.5%).

$^1$H NMR (400 MHz, CD$_3$Cl) δ 8.31 (s, 1H), 7.90 (d, J=7.6 Hz, 1H), 7.83 (m, 2H), 7.78 (d, J=8.8 Hz, 2H), 7.62 (m, 4H), 6.68 (d, J=1.8 Hz, 1H), 6.28 (s, 1H), 1.86 (s, 3H).

APCI-MS $^m$/z: 465.0 [MH$^+$].

Example 1a

6-[1-(4-Cyanophenyl)-1H-pyrazol-5-yl]-5-methyl-3-oxo-4-[3-(trifluoromethyl)phenyl]-3,4-dihydropyrazine-2-carboxamide Form A Ammonia solution (1.12 L, 7M in MeOH, 10 eq) was added to methyl 6-[1-(4-cyanophenyl)-1H-pyrazol-5-yl]-5-methyl-3-oxo-4-[3-(trifluoromethyl)phenyl]-3,4-dihydropyrazine-2-carboxylate (377 g) and MeOH (3.8 L, 10 vols) under nitrogen. The suspension was stirred at ambient temperature for 36 h. The mixture was then filtered, washed with MeOH (2×754 ml) and dried under vacuum. The crude material was dissolved in acetone (10.7 L) at 45° C., and filtered to remove particulates. The filtrate was is concentrated to a volume of about 3.8 L. The resulting slurry was diluted by the addition of methyl isobutyl ketone (10 L), and a further 3.2 L of solvent were removed by distillation. Further methyl isobutyl ketone (7.8 L) was added to achieve a total of about 53 relative volumes (with respect to substrate). The resulting slurry was heated to 53-60° C. and held within this temperature range until in-processes testing (DSC) showed that the desired polymorph had been achieved (62 hours for this particular batch). The slurry was cooled to 25° C. over 4 hours, and then held at 20-25° C. for 36 hours. The product was collected by filtration, and the cake washed with methyl isobutyl ketone (1.9 L). The cake was dried in a vacuum oven at 55° C. until constant weight was achieved. After drying, the title compound (310.8 g, 87%) was obtained as a pale yellow crystalline solid.

$^1$H NMR (400 MHz, CDCl$_3$) δ 8.31 (s, 1H), 7.90 (d, J=7.6 Hz, 1H), 7.83 (m, 2H), 7.78 (d, J=8.8 Hz, 2H), 7.62 (m, 4H), 6.68 (d, J=1.8 Hz, 1H), 6.28 (s, 1H), 1.86 (s, 3H).

APCI-MS $^m$/z: 465.0 [MH$^+$].

Ethyl oxo{[3-(trifluoromethyl)phenyl]amino}acetate

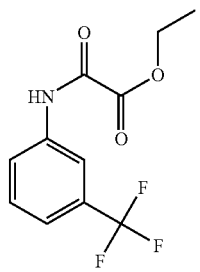 [SMILES: CCOC(=O)C(=O)Nc1cccc(C(F)(F)F)c1]

3-Trifluoromethylaniline (350 g, 1 eq), triethylamine (351 g, 1.6 eq) and ethyl acetate (4.55 L) were charged to a flask, placed under a nitrogen atmosphere and cooled to 0° C. Ethyl oxalyl chloride (356 g, 1.2 eq) was added dropwise keeping the reaction temperature between 5-10° C. The reaction mixture was warmed to 16° C. and held at 16-19° C. for 2.5 hours. The reaction was then quenched with water (2.33 L). The aqueous layer was separated and extracted with ethyl acetate (1.05 L). The organic layers were combined and washed with 2M HCl (0.88 L); water (0.88 L); saturated aqueous sodium bicarbonate (0.58 L); and water (0.88 L). The organic layer was concentrated to dryness to yield the title compound (568.2 g, 100%) as an orange/yellow solid.

$^1$H NMR (300 MHz, DMSO-d$_6$) δ 11.09 (s, 1H), 8.19 (s, 1H), 8.03 (d, J=8.0 Hz, 1H), 7.61 (t, J=8.1 Hz, 1H), 7.51 (d, J=7.8 Hz, 1H), 4.32 (q, J=7.5 Hz, 2H), 1.32 (t, J=7.0 Hz, 3H).

APCI-MS $^m$/z: 262.0 [MH$^+$].

N-(2-Hydroxypropyl)-N'-[3-(trifluoromethyl)-phenyl]ethanediamide

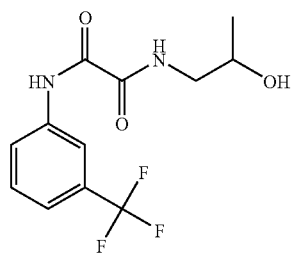 [SMILES: CC(O)CNC(=O)C(=O)Nc1cccc(C(F)(F)F)c1]

Ethanol (1.27 L) and ethyl oxo{[3-(trifluoromethyl)phenyl]amino}acetate (243.15 g, 1 eq) were heated to reflux. 1-Amino-2-propanol (73.2 g, 1.05 eq) in ethanol (0.29 L) was added to the reaction mixture over 1 hour. The reaction mixture was held at reflux for a further 3 hours and then cooled to 20-25° C. The solvent was removed on a rotary evaporator and the resulting white solid was dissolved in ethyl acetate (1.6 L). The solution was reduced in volume by 80% by distillation at atmospheric pressure. Heptane (1.29 L) was then added and the product precipitated. The mixture was cooled further to 0-5° C. and held at this temperature for 1 hour. The mixture was filtered and the filter cake washed with heptane (0.24 L). The damp product was dried at 50° C. for 16 hours in a vacuum oven. The title compound (227.88 g, 84.3%) was isolated as a white crystalline solid.

$^1$H NMR (300 MHz, DMSO-d$_6$) δ 10.99 (bs, 1H), 8.77 (t, J=6.3 Hz, 1H), 8.29 (s, 1H), 8.11 (d, J=8.2 Hz, 1H), 7.60 (t, J=8.1 Hz, 1H), 7.49 (d, J=7.5 Hz, 1H), 4.91 (d, J=4.9 Hz, 1H), 3.78 (p, J=5.7 Hz, 1H), 3.20-3.12 (m, 2H), 1.05 (d, J=6.3 Hz, 3H).

APCI-MS $^m$/z: 273.1 [MH$^+$−18].

N-(2-oxopropyl)-N'-[3-(trifluoromethyl)phenyl]ethanediamide

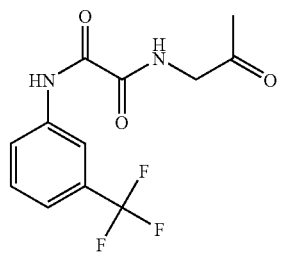 [SMILES: CC(=O)CNC(=O)C(=O)Nc1cccc(C(F)(F)F)c1]

Acetonitrile (3.06 L) and N-(2-hydroxypropyl)-N'-[3-(trifluoromethyl)-phenyl]ethanediamide (200 g, 1 eq) were charged to a reaction vessel to give a white slurry. A slurry of ruthenium chloride hydrate (2.33 g, 0.02 eq) in water (0.21 L) was charged to the reactor. Sodium bromate (114.4 g, 1.1 eq) was dissolved in water (0.48 L) and added dropwise to the dark brown solution over 2 hours keeping the reaction temperature between 20-25° C. The reaction was then held at 20-25° C. for a further 4 hours. Water (3.4 L) was added to the mixture and the product collected by filtration. The filter cake was washed with water (0.84 L) and dried at 65° C. The title compound (177.2 g, 89.2%) was isolated as a pale grey fluffy solid.

$^1$H NMR (300 MHz, DMSO-d$_6$) δ 11.04 (s, 1H), 9.08 (t, J=6.0 Hz, 1H), 8.29 (s, 1H), 8.12 (d, J=8.1 Hz, 1H), 7.61 (t, J=8.1 Hz, 1H), 7.50 (d, J=7.9 Hz, 1H), 4.09 (d, J=6.0 Hz, 2H), 2.14 (s, 3H).

MS$^m$/z: 289 [MH$^+$]

6-Methyl-1-[3-(trifluoromethyl)phenyl]-1,4-dihydropyrazine-2,3-dione

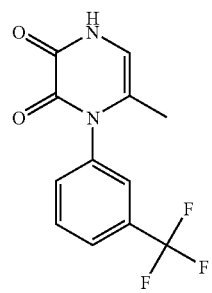 [SMILES: Cc1c[nH]c(=O)c(=O)n1-c1cccc(C(F)(F)F)c1]

Conc. sulphuric acid (2.35 L) was heated to 50-55° C. and N-(2-oxopropyl)-N'-[3-(trifluoromethyl)phenyl]ethanediamide (200 g, 1 eq)) was then added portion-wise over 2 hours to give a clear brown solution. After 3.25 hours the reaction was cooled to 20° C. The reaction mixture was then added to water (6 L), keeping the temperature below 10° C. The white slurry was then stirred at 0-5° C. for a further 1 hour before filtering. The filter cake was washed with water (2 L) and the damp product recharged to the flask. Water (0.85 L) was charged and the mixture stirred for 30 minutes. The mixture was filtered and the filter cake washed with water (0.25 L). The title compound was isolated as a water-wet, off-white solid (228.0 g, water content=26.5%, corrected mass 168.0 g, 90%).

$^1$H NMR (400 MHz, DMSO-d$_6$) δ 11.24 (bs, 1H), 7.87-7.81 (m, 2H), 7.77 (t, J=7.8 Hz, 1H), 7.67 (d, J=7.8 Hz, 1H), 6.30 (d, J=5.2 Hz, 1H), 1.61 (d, J=1.1 Hz, 3H).

APCI-MS $^m$/z: 271.0 [MH$^+$].

3-Bromo-6-methyl-1-[3-(trifluoromethyl)phenyl]pyrazin-2(1H)-one

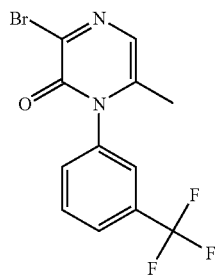 [SMILES: Cc1cnc(Br)c(=O)n1-c1cccc(C(F)(F)F)c1]

6-Methyl-1-[3-(trifluoromethyl)phenyl]-1,4-dihydropyrazine-2,3-dione (289.34 g @ 100%, 1 eq) and toluene (3 L) were charged to a flask and the slurry heated to reflux. Azeotroped water (53 ml) was collected and the slurry cooled to 25° C. The toluene was then removed under reduced pressure at <50° C. to give an off-white powder. This material was then added to acetonitrile (2.95 L) and the reaction mixture heated to 64-67° C. In a separate 2 L 3 necked flask, phosphorus oxybromide (368.4 g, 1.2 eq) was dissolved in acetonitrile (1.475 L). The POBr$_3$/acetonitrile solution was then added to the original flask over 45 minutes at 64-67° C. The reaction mixture was then held at 64-67° C. for 4.5 hours and was then cooled to 20-25° C. Saturated sodium bicarbonate in water (10.3 L) was added over 30 minutes to quench the reaction. The mixture was then stirred for 6 hours at 20-25° C. The solid was then filtered off and the filter-cake washed with water (2×0.55 L) to give the title compound as a water-wet solid (486.4 g, 74.3% @ 100%).

$^1$H NMR (400 MHz, DMSO-d$_6$) δ 7.96 (s, 1H), 7.92 (d, J=7.5 Hz, 1H), 7.83 (t, J=7.5 Hz, 1H), 7.77 (d, J=7.5 Hz, 1H), 7.27 (s, 1H), 1.84 (s, 3H).

APCI-MS $^m$/z: 232.9 and 234.9 [MH$^+$].

Methyl 5-methyl-3-oxo-4-[3-(trifluoromethyl)phenyl]-3,4-dihydropyrazine-2-carboxylate

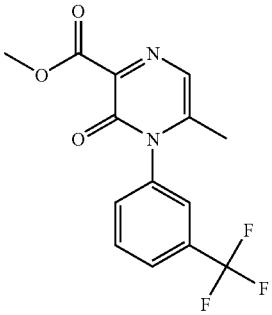 [SMILES: COC(=O)c1ncc(C)n(-c2cccc(C(F)(F)F)c2)c1=O]

3-Bromo-6-methyl-1-[3-(trifluoromethyl)phenyl]pyrazin-2(1H)-one (750 g), diacetoxypalladium (3 g, 0.006 eq), 1,3-bis(diphenylphosphino)propane (6.6 g, 0.007 eq) and triethylamine (600 ml) were dissolved in methanol (3.15 L). The reaction mixture was degassed with carbon monoxide (10 bar) and heated to 65° C. for 12 hours. The reaction mixture was concentrated to two thirds of its volume and cooled to 0° C. The product was filtered, washed three times with methanol and diethyl ether (1 L). The title compound was slurried in water (2 L), filtered and was dried under vacuum to give 590 g (85%).

$^1$H NMR (400 MHz, DMSO-d$_6$) δ 7.97 (s, 1H), 7.92 (d, J=7.5 Hz, 1H), 7.83 (t, J=7.5 Hz, 1H), 7.77 (d, J=7.5 Hz, 1H), 7.52 (s, 1H), 3.80 (s, 3H), 1.94 (s, 3H).

APCI-MS $^m$/z: 313.0 [MH$^+$].

Methyl 6-bromo-5-methyl-3-oxo-4-[3-(trifluoromethyl)phenyl]-3,4-dihydropyrazine-2-carboxylate

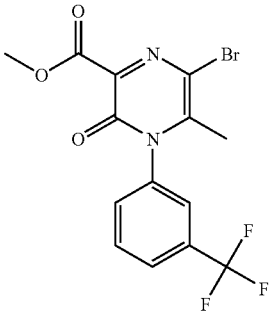 [SMILES: COC(=O)c1nc(Br)c(C)n(-c2cccc(C(F)(F)F)c2)c1=O]

Methyl 5-methyl-3-oxo-4-[3-(trifluoromethyl)phenyl]-3,4-dihydropyrazine-2-carboxylate (400 g, 1 eq) was dissolved in DMF (3 L) and stirred at 17-20° C. N-Bromosuccinimide (229.3 g, 1 eq) was dissolved in DMF (1 L), and added to the ester solution over 1 hour. Post-addition, the reaction was stirred at 17-20° C. for 10 hours. The reaction mixture was added to water (15 L) with stirring. The resulting slurry was stirred at 20-25° C. overnight. The title compound was collected by filtration. The cake was washed with water (1 L) and heptane (1 L) and then dried to constant weight at 40° C. to give 456 g (91%).

¹H NMR (299.947 MHz, DMSO-d₆) δ 7.94 (d, J=6.9 Hz, 2H), 7.86 (t, J=7.8 Hz, 1H), 7.76 (d, J=7.9 Hz, 1H), 3.83 (s, 3H), 2.11 (s, 3H).

4-(1H-pyrazol-1-yl)-benzonitrile

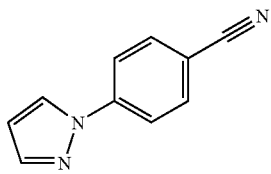 [SMILES: N#Cc1ccc(-n2cccn2)cc1]

4-Fluorobenzonitrile (204.2 g), pyrazole (138.6 g, 1.22 eq) and potassium carbonate (281.5 g, 1.22 eq) in DMF (1110 ml) were heated at 120° C. for 7 hours. The suspension was cooled to 25° C. and water (2920 ml) added. The reaction was extracted with MTBE (3×1460 ml) and the combined extracts were washed with water (3×1460 ml) and saturated aqueous sodium chloride (1460 ml). The organic phase was concentrated at atmospheric pressure until the pot temperature rose to 65° C. Heptane (1700 ml) was added over 30 minutes at 60-65° C., and then a further 300 ml of distillate was collected. The solution was stirred at 60-65° C. for 15 minutes and then cooled to <5° C. The slurry was filtered and washed with heptane (2×200 ml), and dried under vacuum to constant weight to give the title compound as a solid (245.3 g, 87%).

¹H NMR (400 MHz, CDCl₃): 6.51 (q, 1H), 7.71 (d, 2H), 7.75 (d, 1H), 7.81 (d, 2H), 7.98 (d, 1H).

4-[5-(4,4,5,5-Tetramethyl-[1,3,2]dioxaborolan-2-yl)-pyrazol-1-yl]-benzonitrile

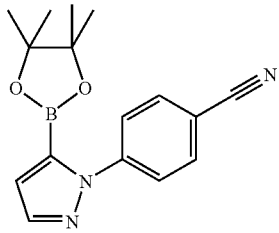 [SMILES: CC1(C)OB(c2ccnn2-c2ccc(C#N)cc2)OC1(C)C]

2,2,6,6-Tetramethylpiperidine (623.4 ml, 1.25 eq) and THF (2.5 L) were added to a flask and cooled to −20±2° C. Hexyl lithium (2.3M, 1.542 L, 1.2 eq) was added over 140 minutes whilst maintaining the internal temperature at −20±2° C. After complete addition, the reaction mixture was stirred at −20±2° C. for 30 minutes. The mixture was then cooled to −50±2° C., and a solution of benzonitrile (325 ml) in THF (2.4 L) was then added slowly over 143 minutes whilst keeping the temperature at −50±2° C. After addition was complete, the mixture was stirred at −50±2° C. for 2.5 hours. Isopropyl pinacol borate (2-isopropoxy-4,4,5,5-tetramethyl-1,3,2-dioxaborolane) (753.4 ml, 1.25 eq) was added to the reaction mixture over 66 minutes whilst keeping the temperature at −50±2° C., followed by a line-wash of THF (0.3 L). After addition was complete, the mixture was left to stir for 45 minutes. The mixture was then allowed to warm to −15° C. Acetic acid (0.51 L, 1 eq) was added over 45 minutes whilst keeping the temperature <0° C. The mixture was then stirred for 30 minutes at 0 to −5° C. Water (1.5 L) was then added over 1.5 hours whilst keeping the temperature between 0 and −5° C., followed by the further water (4.5 L) over 1 hour. After the water addition was complete, the mixture was stirred between 0 and −5° C. for 30 minutes. The solid was filtered off, washed four times with cold water (1000 mL) and then dried in a vacuum oven at 40° C. to constant weight to give 4-[5-(4,4,5,5-tetramethyl-[1,3,2]dioxaborolan-2-yl)-pyrazol-1-yl]-benzonitrile (566 g, 64%).

¹H NMR (300 MHz, CDCl₃): 1.30 (s, 12H), 6.97 (d, 1H), 7.73 (m, 5H).

Methyl 6-[1-(4-cyanophenyl)-1H-pyrazol-5-yl]-5-methyl-3-oxo-4-[3-(trifluoromethyl)phenyl]-3,4-dihydropyrazine-2-carboxylate

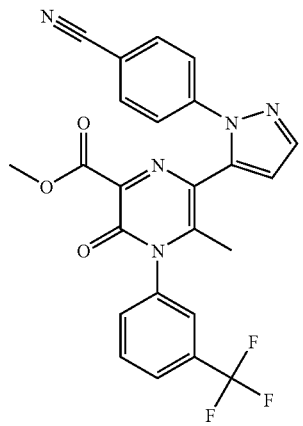 [SMILES: COC(=O)c1nc(-c2ccnn2-c2ccc(C#N)cc2)c(C)n(-c2cccc(C(F)(F)F)c2)c1=O]

1-yl]-benzonitrile (503 g, 1.536 eq), sodium acetate (273.1 g, 3 eq), dichloro 1,1-bis(di-tert-butylphosphino)ferrocene palladium (36.1 g, 0.05 eq) and DMF (4.35 L) were charged to a reaction vessel under an inert atmosphere, and heated to 50° C. Once at temperature, water (20 ml, 1 eq) was added, and the mixture was stirred for 9 hours. The reaction mixture was allowed to cool to 20-25° C., and was then added to water (21.8 L) over a 2 hour period. The mixture was stirred at 20-25° C. for 30 minutes, and the product was then isolated by filtration. The cake was washed with water (2×4.3 L) and tert-butyl methyl ether (2×4.3 L) and was then dried overnight under vacuum at 20-25° C. to give the crude title compound (493 g).

The crude product (493 g) was further purified by dissolution in acetonitrile (9.7 L) and passage through two CUNO filters. The filters were washed with acetonitrile (2×5 L). The combined organic phases were treated with Smopex® 111 scavenger (98.6 g), stirring at 50° C. for 10 hours before filtering through silica (60 Å, 230-400 mesh, 2.46 Kg). The silica was washed again with acetonitrile (2×4.9 L).

The combined acetonitrile solutions were concentrated to about 2.5 L. Tert-butyl methyl ether (5 L) was added, and then removed by distillation. This process was repeated twice more. The resulting slurry was filtered, and the product washed with tert-butyl methyl ether (1 L) to give the pure title compound (398.5 g, 73%).

¹H NMR (300 MHz, CDCl₃) δ 7.82-7.80 (m, 2H), 7.75-7.70 (m, 3H), 7.58-7.53 (m, 2H), 7.44 (s, 1H), 7.34 (d, J=7.9 Hz, 1H), 6.63 (d, J=1.7 Hz, 1H), 3.92 (s, 3H), 1.82 (s, 3H).

Example 2

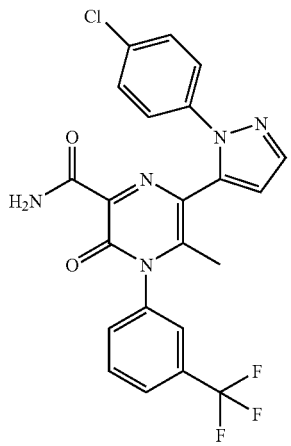 [SMILES: Cc1c(-c2ccnn2-c2ccc(Cl)cc2)nc(C(N)=O)c(=O)n1-c1cccc(C(F)(F)F)c1]

6-[1-(4-Chlorophenyl)-1H-pyrazol-5-yl]-5-methyl-3-oxo-4-[3-(trifluoromethyl)phenyl]-3,4-dihydropyrazine-2-carboxamide 1-(4-Chlorophenyl)-1H-pyrazole was prepared from 1-bromo-4-chlorobenzene and pyrazole according to the procedure of Cristau et al., *Eur. J. Org. Chem.* 2004, 4, 695-709.

$^1$H NMR (400 MHz, DMSO-d$_6$) δ 8.53 (d, J=2.4 Hz, 1H), 7.88 (d, J=9.6 Hz, 2H), 7.76 (d, J=2.1 Hz, 1H), 7.55 (d, J=9.2 Hz, 2H), 6.56 (t, J=2.1 Hz, 1H) ppm.

APCI-MS m/z 179.1 (main fragment) [MH$^+$].

In a dry flask, 2,2,6,6-tetramethylpiperidine (0.30 mL, 1.8 mmol) in anhydrous THF (10 mL) under argon was treated with a 1.6M solution of n-butyllithium in hexanes (1.1 mL, 1.8 mmol) at −76° C. during 2 minutes. After stirring for 5 minutes at −76° C., a solution of 1-(4-chlorophenyl)-1H-pyrazole (0.21 g, 1.1 mmol) in anhydrous THF (2 mL) was added over 4 minutes. After stirring for 20 minutes at −76° C., tributyltin chloride (0.30 mL, 1.11 mmol) was added all at once. The resulting mixture was stirred at −76° C. for 10 minutes and at ambient temperature for 5 minutes, then quenched by addition of methanol (1 mL). The mixture was concentrated by rotary evaporation, the residue was taken up in water (20 mL) and washed with ethyl acetate (20 mL). The organic phase was separated, washed with brine (10 mL), dried over anhydrous sodium sulfate, filtered and concentrated by rotary evaporation. Purification of the crude product by flash chromatography on silica with ethyl acetate/n-heptane (1:7) as eluent gave 1-(4-chlorophenyl)-5-tributylstannyl-1H-pyrazole (0.20 g, 40%) as a colourless oil.

$^1$H NMR (300 MHz, DMSO-d$_6$) δ 7.77 (d, J=1.7 Hz, 1H), 7.62 (d, J=8.7 Hz, 2H), 7.42 (d, J=8.7 Hz, 2H), 6.54 (d, J=1.7 Hz, 1H), 1.40-1.10 (m's, 12H), 0.97-0.85 (m, 6H), 0.79 (t, J=7.2 Hz, 9H) ppm.

APCI-MS m/z 469.1 (main fragment) [MH$^+$].

Methyl 6-iodo-5-methyl-3-oxo-4-[3-(trifluoromethyl)phenyl]-3,4-dihydropyrazine-2-carboxylate (SM1, 0.133 g, 0.304 mmol), 1-(4-chlorophenyl)-5-tributylstannyl-1H-pyrazole (0.16 g, 0.33 mmol), bis(triphenylphosphine)palladium(II) chloride (0.011 g, 0.015 mmol) and anhydrous THF (1.5 mL) in a vial were heated three consecutive times (for 55 minutes in total) in a microwave reactor (Biotage) at 130° C. until most of the iodo SM was consumed. The dark solution was concentrated to dryness with silica and applied to a silica column. Flash chromatography with ethyl acetate/n-heptane (1:4 through 2:1) gave methyl 6-[2-(4-chlorophenyl)pyrazol-3-yl]-5-methyl-3-oxo-4-[3-(trifluoromethyl)phenyl]-3,4-dihydropyrazine-2-carboxylate (0.0915 g, 62%) as an off-white solid.

$^1$H NMR (400 MHz, CD$_3$CN) δ 7.88 (d, J=8.0 Hz, 1H), 7.80 (t, J=8.0 Hz, 1H), 7.76 (d, J=2.1 Hz, 1H), 7.66 (br s, 1H), 7.58 (d, J=8.0 Hz, 1H), 7.44 (m, 4H), 6.61 (d, J=2.1 Hz, 1H), 3.81 (s, 3H), 1.83 (s, 3H) ppm.

APCI-MS m/z 489.0 (main fragment) [MH$^+$].

Methyl 6-[1-(4-chlorophenyl)-pyrazol-5-yl]-5-methyl-3-oxo-4-[3-(trifluoromethyl)phenyl]-3,4-dihydropyrazine-2-carboxylate (0.0915 g, 0.187 mmol) was dissolved in 7M ammonia in methanol (4.0 mL, 28 mmol) and heated in a microwave reactor (Biotage) at 60° C. for 7 minutes. The violet coloured solution was concentrated by rotary evaporation. The crude product was purified by semi-preparative reversed phase-HPLC (Kromasil C18 column) with acetonitrile-water (60 to 97% MeCN) as eluent to give 6-[1-(4-chlorophenyl)-1H-pyrazol-5-yl]-5-methyl-3-oxo-4-[3-(trifluoromethyl)phenyl]-3,4-dihydropyrazine-2-carboxamide (0.0636 g, 72%) as a light yellow solid.

$^1$H NMR (400 MHz, CD$_3$CN) δ 8.33 (br s, 1H), 7.89 (d, J=8.0 Hz, 1H), 7.81 (t, J=8.0 Hz, 1H), 7.78 (d, J=1.8 Hz, 1H), 7.64 (br s, 1H), 7.56 (d, J=8.0 Hz, 1H), 7.43 (br s, 4H), 6.63 (d, J=1.8 Hz, 1H), 6.28 (br s, 1H), 1.82 (s, 3H) ppm.

APCI-MS m/z 473.9 (main fragment) [MH$^+$].

Example 3

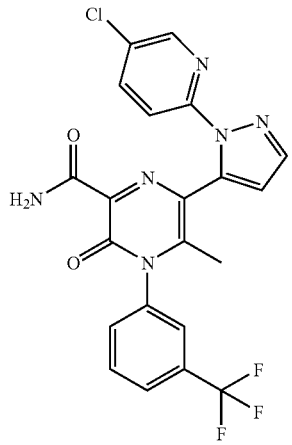 [SMILES: Cc1c(-c2ccnn2-c2ccc(Cl)cn2)nc(C(N)=O)c(=O)n1-c1cccc(C(F)(F)F)c1]

6-[1-(5-Chloropyridin-2-yl)-1H-pyrazol-5-yl]-5-methyl-3-oxo-4-[3-(trifluoromethyl)phenyl]-3,4-dihydropyrazine-2-carboxamide The title compound was synthesised using an analogous route to that described for Example 1.

$^1$H NMR (400 MHz, DMSO-d$_6$) δ 8.47 (d, J=2.5 Hz, 1H), 8.25 (bs, 1H), 8.09 (dd, J=8.1/2.5 Hz, 1H), 7.99-7.79 (m, 7H), 7.72 (bs, 1H), 6.73 (d, J=1.7 Hz, 1H), 1.85 (s, 3H).

APCI-MS $^m$/z: 475.0 [MH$^+$].

Example 4

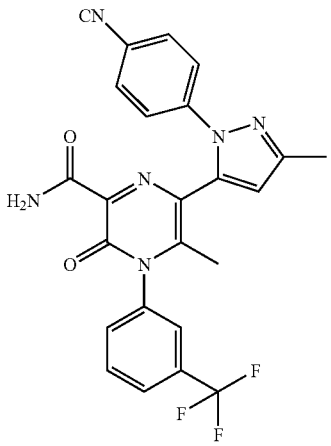 [SMILES: Cc1cc(-c2nc(C(N)=O)c(=O)n(-c3cccc(C(F)(F)F)c3)c2C)n(-c2ccc(C#N)cc2)n1]

6-[1-(4-Cyanophenyl)-3-methyl-1H-pyrazol-5-yl]-5-methyl-3-oxo-4-[3-(trifluoromethyl)phenyl]-3,4-dihydropyrazine-2-carboxamide The title compound was synthesised using an analogous route to that described for Example 1.

$^1$H NMR (400 MHz, DMSO-$d_6$) δ 8.07 (bs, 1H), 7.96-7.83 (m, 5H), 7.77 (d, J=8.1 Hz, 1H), 7.69 (bs, 1H), 7.62 (d, J=8.8 Hz, 2H), 6.57 (s, 1H), 2.33 (s, 3H), 1.85 (s, 3H).

APCI-MS $^m$/z: 479.1 [MH$^+$].

Example 5

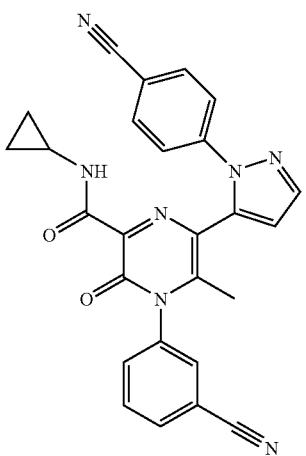 [SMILES: Cc1c(-c2ccnn2-c2ccc(C#N)cc2)nc(C(=O)NC2CC2)c(=O)n1-c1cccc(C#N)c1]

4-(3-Cyanophenyl)-6-[1-(4-cyanophenyl)-1H-pyrazol-5-yl]-N-cyclopropyl-5-methyl-3-oxo-3,4-dihydropyrazine-2-carboxamide The title compound was synthesised using an analogous route to that described for Example 2.

$^1$H NMR (300 MHz, DMSO-$d_6$) δ 0.42 (dt, 2H), 0.68 (td, 1H), 1.90 (s, 2H), 2.76 (quintet, 1H), 3.32 (s, 3H), 6.75 (d, 1H), 7.65 (dt, 2H), 7.77-7.93 (m, 4H), 8.02 (d, 1H), 8.06 (dt, 1H), 8.65 (d, 1H).

APCI-MS $^m$/z: 462.1 [MH$^+$].

Example 6

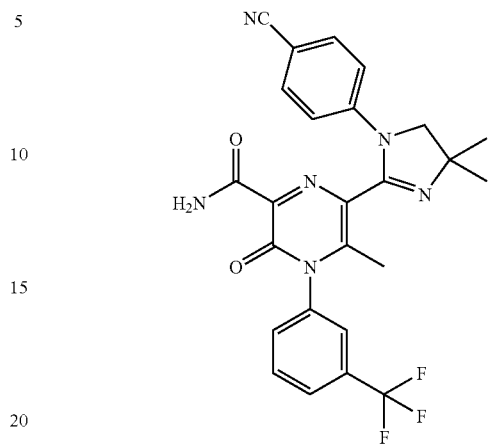

6-(1-(4-Cyanophenyl)-4,4-dimethyl-4,5-dihydro-1H-imidazol-2-yl)-5-methyl-3-oxo-4-(3-(trifluoromethyl)phenyl)-3,4-dihydropyrazine-2-carboxamide 4-Fluorobenzonitrile (7.0 g, 58 mmol) and 2-methylpropane-1,2-diamine (14 g, 160 mmol) were heated in a sealed vial in a microwave reactor (Biotage) at 180° C. for 25 minutes in two batches. Each batch was dissolved in methanol (50 mL) and then concentrated with silica to dryness. Flash chromatography on silica of each batch with neat acetonitrile and 2% triethylamine in acetonitrile as eluents gave 4-(2-amino-2-methylpropylamino)benzonitrile (9.58 g, 88% combined yield) as a white solid.

$^1$H NMR (400 MHz, DMSO-$d_6$) δ 7.41 (d, J=8.8 Hz, 2H), 6.71 (d, J=8.8 Hz, 2H), 6.49 (t, J=6.0 Hz, 1H), 2.93 (d, J=6.0 Hz, 2H), 1.04 (s, 6H) ppm.

APCI-MS m/z 190.0 [MH$^+$].

In a bomb tube of stainless steel (Parr) fitted with an internal cylindrical glass vessel and magnetic stirrer, methyl 6-iodo-5-methyl-3-oxo-4-(3-(trifluoromethyl)phenyl)-3,4-dihydropyrazine-2-carboxylate (SM1, 1447 mg, 3.3 mmol), 4-(2-amino-2-methylpropylamino)benzonitrile (750 mg, 4.0 mmol), triethylamine (3.2 mL, 23 mmol) and acetonitrile (35 mL) were mixed. The mixture was purged with argon for 10 minutes. After adding bis(tributylphosphine)palladium (120 mg, 0.23 mmol), the bomb tube was sealed, evacuated and back-filled with carbon monoxide five consecutive times. The contents of the bomb tube were stirred under carbon monoxide (6.5 bar) at 50° C. for 9 h. LC-MS indicated about 50% conversion to desired product and unreacted SM. The dark red-brown solution was concentrated to dryness, dissolved in ethyl acetate (200 mL), washed with water (2×50 mL), dried over anhydrous sodium sulfate, filtered and concentrated with silica to dryness. Flash chromatography on silica with ethyl acetate/n-heptane (1:3 and 1:1) as eluents gave methyl 6-(1-(4-cyanophenylamino)-2-methylpropan-2-ylamino)-5-methyl-3-oxo-4-(3-(trifluoromethyl)phenyl)-3,4-dihydropyrazine-2-carboxylate (0.38 g, 22%) as a yellow solid.

$^1$H NMR (400 MHz, DMSO-$d_6$) δ 7.93 (d, J=8.8 Hz, 1H), 7.92 (br s, 1H), 7.85 (t, J=8.4 Hz, 1H), 7.75 (br s, 1H), 7.74 (d, J=8.8 Hz, 1H), 7.42 (d, J=8.8 Hz, 2H), 6.76 (d, J=8.8 Hz, 2H), 6.67 (t, J=6.4 Hz, 1H), 3.82 (s, 3H), 3.48 (d, J=6.4 Hz, 2H), 2.36 (s, 3H), 1.41 (s, 6H) ppm.

APCI-MS m/z 528.0 (main fragment) [MH+].

Phosphorous pentoxide (0.81 g, 5.7 mmol) was added in one portion to a stirred solution of methyl 6-(1-(4-cyanophenylamino)-2-methylpropan-2-ylcarbamoyl)-5-methyl-3-oxo-4-(3-(trifluoromethyl)phenyl)-3,4-dihydropyrazine-2-carboxylate (0.50 g, 0.95 mmol) and dry acetonitrile (10 mL) under argon at 60° C. After 1.5 h, the reaction mixture was cooled to ambient temperature and poured into a stirred mixture of ethyl acetate (50 mL), saturated sodium bicarbonate (30 mL) and water (10 mL). The organic phase was separated and the is aqueous phase was washed repeatedly with ethyl acetate (3×50 mL). The organic phases were combined, washed with brine (1×40 mL), dried over anhydrous sodium sulfate, filtered and concentrated to dryness to give a light-brown glass (0.633 g). Purification by preparative HPLC (XBridge column) with 40 to 95% acetonitrile in water as eluent gave methyl 6-(1-(4-cyanophenyl)-4,4-dimethyl-4,5-dihydro-1H-imidazol-2-yl)-5-methyl-3-oxo-4-(3-(trifluoromethyl)phenyl)-3,4-dihydropyrazine-2-carboxylate (0.259 g, 54%) as a beige solid.

$^1$H NMR (400 MHz, DMSO-$d_6$) δ 8.06 (br s, 1H), 8.02 (br s, 1H), 7.96 (d, J=8.0 Hz, 1H), 7.87 (t, J=8.0 Hz, 1H), 7.82 (d, J=8.0 Hz, 1H), 7.69 (br s, 1H), 7.61 (d, J=8.8 Hz, 2H), 6.96 (d, J=8.8 Hz, 2H), 3.836 (d, $J_{AB}$=9.6 Hz, 1H), 3.782 (d, $J_{BA}$=9.6 Hz, 1H), 2.10 (s, 3H), 1.33 (s, 3H), 1.31 (s, 3H) ppm.

APCI-MS m/z 510.0 (main fragment) [MH+].

Methyl 6-(1-(4-cyanophenyl)-4,4-dimethyl-4,5-dihydro-1H-imidazol-2-yl)-5-methyl-3-oxo-4-(3-(trifluoromethyl)phenyl)-3,4-dihydropyrazine-2-carboxylate (0.26 g, 0.51 mmol) in methanol (5 mL) and 7.0M ammonia in methanol (14 mL, 98 mmol) were stirred in a sealed glass tube at 60° C. for 60 minutes and at RT for 45 minutes. The solution was concentrated by rotary evaporation to give a crude product as a dark-red film. Purification by preparative reversed phase-HPLC (XTerra™ column) with acetonitrile-water (ammonia added) as eluent gave a yellow solid (0.156 g). The product was stirred with absolute ethanol (2.8 mL) in a sealed vial at 60° C. for 3.5 h, at 40° C. overnight and at RT overnight. The solid product was filtered off, washed with small volumes of absolute ethanol and dried at 65° C. and 0.1 mmHg overnight to give 6-(1-(4-cyanophenyl)-4,4-dimethyl-4,5-dihydro-1H-imidazol-2-yl)-5-methyl-3-oxo-4-(3-(trifluoromethyl)phenyl)-3,4-dihydropyrazine-2-carboxamide (0.116 g, 48%) as a light yellow solid. HPLC-purity: 99-100%.

$^1$H NMR (400 MHz, DMSO-$d_6$) δ 8.03 (br s, 1H), 8.02 (br s, 1H), 7.96 (d, J=8.0 Hz, 1H), 7.87 (t, J=8.0 Hz, 1H), 7.82 (d, J=8.0 Hz, 1H), 7.69 (br s, 1H), 7.61 (d, J=8.8 Hz, 2H), 6.96 (d, J=8.8 Hz, 2H), 3.847 (d, $J_{AB}$=9.6 Hz, 1H), 3.795 (d, $J_{BA}$=9.6 Hz, 1H), 2.10 (s, 3H), 1.33 (s, 3H), 1.31 (s, 3H) ppm.

APCI-MS m/z 495.1 (main fragment) [MH+].

Starting Material SM1

Methyl 6-iodo-5-methyl-3-oxo-4-[3-(trifluoromethyl)phenyl]-3,4-dihydropyrazine-2-carboxylate 3-Trifluoromethylaniline (5.0 g, 31 mmol) and triethylamine (3.54 g, 35 mmol) were dissolved in DCM (60 ml, dried). The mixture was cooled on ice and to the stirred solution was added dropwise a solution of ethyl oxalyl chloride (4.36 g, 32 mmol) in DCM (15 ml). After complete addition, the reaction was allowed to stand for 10 minutes. The reaction mixture was washed with water (50 ml), then washed with brine (30 ml), and the organic phase was dried over $Na_2SO_4$. Filtration and evaporation gave ethyl oxo{[3-(trifluoromethyl)phenyl]amino}acetate (8.04 g, 99%) as a white solid.

$^1$H NMR (300 MHz, DMSO-$d_6$) δ 11.09 (s, 1H), 8.19 (s, 1H), 8.03 (d, J=8.0 Hz, 1H), 7.61 (t, J=8.1 Hz, 1H), 7.51 (d, J=7.8 Hz, 1H), 4.32 (q, J=7.5 Hz, 2H), 1.32 (t, J=7.0 Hz, 3H);

APCI-MS $^m$/z: 262.0 [MH+].

Ethyl oxo{[3-(trifluoromethyl)-phenyl]amino}acetate (8.04 g, 30.7 mmol) was dissolved in ethanol (50 ml, 99.5%). To the stirred solution was added 1-amino-2-propanol (racemic, 2.32 g, 31 mmol) in one portion, and the mixture was heated to reflux for 90 minutes. The mixture was allowed to cool and was evaporated to dryness, giving N-(2-hydroxypropyl)-N'-[3-(trifluoromethyl)-phenyl]ethanediamide (8.80 g, 99%) as a white solid.

$^1$H NMR (300 MHz, DMSO-$d_6$) δ 10.99 (bs, 1H), 8.77 (t, J=6.3 Hz, 1H), 8.29 (s, 1H), 8.11 (d, J=8.2 Hz, 1H), 7.60 (t, J=8.1 Hz, 1H), 7.49 (d, J=7.5 Hz, 1H), 4.91 (d, J=4.9 Hz, 1H), 3.78 (p, J=5.7 Hz, 1H), 3.20-3.12 (m, 2H), 1.05 (d, J=6.3 Hz, 3H);

APCI-MS $^m$/z: 273.1 [MH+-18].

N-(2-Hydroxypropyl)-N'-[3-(trifluoromethyl)phenyl]-ethanediamide (2.2 g, 7.58 mmol) was dissolved in $CH_3CN$ (50 ml) and water (7 ml). To the stirred solution was added $NaBrO_3$ (1.15 g, 7.58 mmol) and a solution of $RuCl_3 \cdot xH_2O$ in $CH_3CN$ (3 ml). The mixture was stirred for 1 h, and the reaction was monitored by LC-MS and TLC. The organic solvent was removed in vacuo, and the residue was partitioned between DCM (200 ml) and water (200 ml). The organic phase was dried with $Na_2SO_4$ and upon filtration and evaporation N-(2-oxopropyl)-N'-[3-(trifluoromethyl)phenyl]ethanediamide (2.0 g, 91%) was obtained as a grey-white solid.

$^1$H NMR (300 MHz, DMSO-$d_6$) δ 11.04 (s, 1H), 9.08 (t, J=6.0 Hz, 1H), 8.29 (s, 1H), 8.12 (d, J=8.1 Hz, 1H), 7.61 (t, J=8.1 Hz, 1H), 7.50 (d, J=7.9 Hz, 1H), 4.09 (d, J=6.0 Hz, 2H), 2.14 (s, 3H).

N-(2-Oxopropyl)-N'-[3-(trifluoromethyl)phenyl]ethanediamide (1.6 g, 5.5 mmol) and glacial acetic acid (15 ml) were placed in a vial (20 ml). To this solution was added concentrated sulfuric acid (40 drops), and the flask was sealed, and heated with stirring to 100° C. for 90 minutes. Another 40 drops of sulfuric acid was added, and the reaction was allowed to proceed for another 90 minutes. The reaction mixture was allowed to cool, and acetic acid was removed in vacuo. The residue was partitioned between EtOAc (60 ml) and water (40 ml). The aqueous phase was neutralized by addition of NaOH solution to pH 6 to 7. The organic phase was dried, and upon filtration and evaporation a crude product was obtained, which was purified on silica giving 6-methyl-1-[3-(trifluoromethyl)phenyl]-1,4-dihydropyrazine-2,3-dione (1.1 g, 74%) as a yellowish solid.

$^1$H NMR (400 MHz, DMSO-$d_6$) δ 11.24 (bs, 1H), 7.87-7.81 (m, 2H), 7.77 (t, J=7.8 Hz, 1H), 7.67 (d, J=7.8 Hz, 1H), 6.30 (d, J=5.2 Hz, 1H), 1.61 (d, J=1.1 Hz, 3H);

APCI-MS $^m$/z: 271.0 [MH+].

6-Methyl-1-[3-(trifluoromethyl)phenyl]-1,4-dihydropyrazine-2,3-dione (0.52 g, 1.92 mmol) and 1,2-dichloroethane (10 ml) were placed in a vial (20 ml). To the resulting suspension was added carefully oxalyl bromide (0.53 ml, 1.24 g, 5.75 mmol). A foam was formed during the addition, and as the foam was settling down the stirring was started. DMF (3 drops) was added and the vial was sealed and the mixture was stirred overnight. Another portion of oxalyl bromide (0.2 ml, 0.46 g, 2.23 mmol) and DMF (3 drops) was added and the reaction was run for another 24 h. The mixture was partitioned between is DCM (20 ml) and water (20 ml) and the organic phase was dried. Filtration and evaporation gave a crude product, which was purified on silica, affording 3-bromo-6-methyl-1-[3-(trifluoromethyl)phenyl]pyrazin-2 (1H)-one (0.59 g, 93%).

$^1$H NMR (400 MHz, DMSO-$d_6$) δ 7.96 (s, 1H), 7.92 (d, J=7.5 Hz, 1H), 7.83 (t, J=7.5 Hz, 1H), 7.77 (d, J=7.5 Hz, 1H), 7.27 (s, 1H), 1.84 (s, 3H);

APCI-MS $^m$/z: 232.9 and 234.9 [MH$^+$].

A high-pressure steel reactor (Parr) with CO-gas inlet was charged with 3-bromo-6-methyl-1-[3-(trifluoromethyl)phenyl]pyrazin-2(1H)-one (0.25 g, 0.75 mmol), Pd(OAc)$_2$ (0.015 g, 0.067 mmol), PPh$_3$ (0.030 g, 0.11 mmol) and methanol (25 ml). To this mixture was added triethylamine (0.5 ml, 0.36 g, 3.6 mmol), and a magnetic stirrer bar. The reactor was ventilated with CO, and 6 atmospheres CO-pressure was applied to the system. The reactor was heated with stirring to 90° C., and the mixture was stirred vigorously and the reaction was allowed to proceed for 4 h. The volatiles were removed in vacuo and the crude product was purified on silica, to give methyl 5-methyl-3-oxo-4-[3-(trifluoromethyl)phenyl]-3,4-dihydropyrazine-2-carboxylate (0.11 g, 47%) as a solid.

$^1$H NMR (400 MHz, DMSO-$d_6$) δ 7.97 (s, 1H), 7.92 (d, J=7.5 Hz, 1H), 7.83 (t, J=7.5 Hz, 1H), 7.77 (d, J=7.5 Hz, 1H), 7.52 (s, 1H), 3.80 (s, 3H), 1.94 (s, 3H);

APCI-MS $^m$/z: 313.0 [MH$^+$].

Methyl 5-methyl-3-oxo-4-[3-(trifluoromethyl)phenyl]-3,4-dihydropyrazine-2-carboxylate (1.5 g, 4.8 mmol), dry DCM (7.0 mL), trifluoroacetic acid (3.0 mL) and N-iodosuccinimide (1.0 g, 4.5 mmol) were mixed and stirred at RT in the dark (flask covered with aluminum foil). After 5 h, water (5 mL) was added and the mixture was concentrated by rotary evaporation. Water (3 mL) was added once more and the mixture was concentrated as described above. The resulting mixture was diluted with acetonitrile to a total volume of 50 mL. Purification by preparative HPLC with acetonitrile-water as eluent (neutral eluent) gave methyl 6-iodo-5-methyl-3-oxo-4-[3-(trifluoromethyl)phenyl]-3,4-dihydropyrazine-2-carboxylate (0.905 g, 46%) as a yellow crystalline solid.

$^1$H NMR (400 MHz, DMSO-$d_6$) δ 7.93 (br s, 1H), 7.92 (d, J=7.6 Hz, 1H), 7.84 (t, J=7.6 is Hz, 1H), 7.75 (d, J=7.6 Hz, 1H), 3.82 (s, 3H), 2.14 (s, 3H).

APCI-MS m/z 438.8 (MH$^+$).

Starting Material SM2

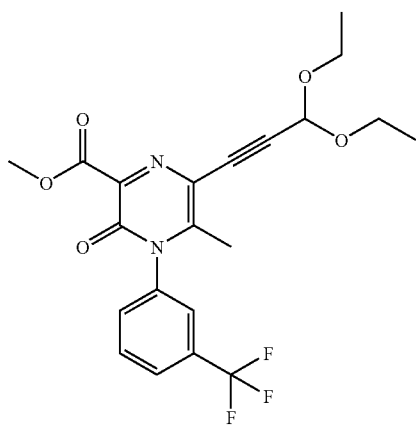 [SMILES: CCOC(C#Cc1nc(C(=O)OC)c(=O)n(-c2cccc(C(F)(F)F)c2)c1C)OCC]

Methyl 6-(3,3-diethoxyprop-1-ynyl)-5-methyl-3-oxo-4-[3-(trifluoromethyl)phenyl]-3,4-dihydropyrazine-2-carboxylate Methyl 6-iodo-5-methyl-3-oxo-4-[3-(trifluoromethyl)phenyl]-3,4-dihydropyrazine-2-carboxylate (SM1, 1.2 g, 2.8 mmol), allylpalladium(II) chloride dimer (0.0072 g), 10% by weight tri(tert-butyl)phosphine in hexane (2.1 mL) and anhydrous DMF (3.0 mL) were stirred until a clear solution was obtained. Propargylaldehyde diethyl acetal (0.44 mL, 3.1 mmol) in anhydrous DMF (2.3 mL) was added, followed by 1,4-diazabicyclo[2.2.2]octane (0.63 g, 5.6 mmol) in small portions. The red solution was purged with dry argon for 5 minutes and then stirred under argon at RT. After 4 h, the solvent was evaporated off using an oil pump. The residue was taken up in acetonitrile (10 mL), filtered through glass-wool and then concentrated with silica. Chromatography on silica with ethyl acetate-heptanes (1:10 and 1:2) as eluents gave the title compound (0.46 g, 37%) as a yellow oil.

$^1$H NMR (400 MHz, CD$_2$Cl$_2$) δ 7.84 (d, J=8.8 Hz, 1H), 7.77 (d, J=8.0 Hz, 1H), 7.49 (br s, 1H), 7.43 (d, J=8.4 Hz, 1H), 5.47 (s, 1H), 3.92 (s, 3H), 3.80-3.71 (m, 2H), 3.68-3.58 (m, 2H), 2.20 (s, 3H), 1.23 (t, J=7.2 Hz, 6H).

APCI-MS m/z 439 (MH$^+$), 393 (M-45).

Human Neutrophil Elastase Quenched-FRET Assay

The assay uses Human Neutrophil Elastase (HNE) purified from serum (Calbiochem art. 324681; Ref. Baugh, R. J. et al., 1976, Biochemistry. 15, 836-841). HNE was stored in 50 mM sodium acetate (NaOAc), 200 mM sodium chloride (NaCl), pH 5.5 with added 30% glycerol at −20° C. The protease substrate used was Elastase Substrate V Fluorogenic, MeO-Suc-AAPV-AMC (Calbiochem art. 324740; Ref. Castillo, M. J. et al., 1979, Anal. Biochem. 99, 53-64). The substrate was stored in dimethyl sulphoxide (DMSO) at −20° C. The assay additions were as follows: Test compounds and controls were added to black 96-well flat-bottom plates (Greiner 655076), 1 μL in 100% DMSO, followed by 30 μL HNE in assay buffer with 0.01% Triton (trade mark) X-100 detergent. The assay buffer constitution was: 100 mM Tris(hydroxymethyl)aminomethane (TRIS) (pH 7.5) and 500 mM NaCl. The enzyme and the compounds were incubated at room temperature for 15 minutes. Then 30 μl substrate in assay buffer was added. The assay was incubated for 30 minutes at room temperature. The concentrations of HNE enzyme and substrate during the incubation were 1.7 nM and 100 μM, respectively. The assay was then stopped by adding 60 W stop solution (140 mM acetic acid, 200 mM sodium monochloroacetate, 60 mM sodium acetate, pH 4.3). Fluorescence was measured on a Wallac 1420 Victor 2 instrument at settings: Excitation 380 nm, Emission 460 nm. IC$_{50}$ values were determined using Xlfit curve fitting using model 205.

When tested in the above screen, the compounds of the Examples gave IC$_{50}$ values for inhibition of human neutrophil elastase activity of less than 30 μM (micromolar), indicating that the compounds of the invention are expected to possess useful therapeutic properties. Specimen results are shown in the following Table:

| Compound | Inhibition of Human Neutrophil Elastase IC$_{50}$ (nanomolar, nM) |
| --- | --- |
| Example 1 or 1a | 2.2 |
| Example 2 | 11 |
| Example 3 | 28 |

-continued

| Compound | Inhibition of Human Neutrophil Elastase IC$_{50}$ (nanomolar, nM) |
|---|---|
| Example 4 | 3.5 |
| Example 5 | 4.2 |
| Example 6 | 1.4 |

The invention claimed is:

1. A compound being 6-[1-(4-cyanophenyl)-1H-pyrazol-5-yl]-5-methyl-3-oxo-4-[3-(trifluoromethyl)phenyl]-3,4-dihydropyrazine-2-carboxamide, or a pharmaceutically acceptable salt or polymorph thereof.

2. A polymorph of a compound according to claim 1 being 6-[1-(4-cyanophenyl)-1H-pyrazol-5-yl]-5-methyl-3-oxo-4-[3-(trifluoromethyl)phenyl]-3,4-dihydropyrazine-2-carboxamide Form A.

3. A pharmaceutical composition comprising a compound or a pharmaceutically acceptable salt or polymorph thereof as claimed in claim 2 in association with a pharmaceutically acceptable adjuvant, diluent or carrier.

4. A compound according to claim 1, being 6-[1-(4-cyanophenyl)-1H-pyrazol-5-yl]-5-methyl-3-oxo-4-[3-(trifluoromethyl)phenyl]-3,4-dihydropyrazine-2-carboxamide.

5. A compound according to claim 2, being a pharmaceutically acceptable salt of 6-[1-(4-cyanophenyl)-1H-pyrazol-5-yl]-5-methyl-3-oxo-4-[3-(trifluoromethyl)phenyl]-3,4-dihydropyrazine-2-carboxamide.

6. A polymorph of a compound according to claim 1, being 6-[1-(4-cyanophenyl)-1H-pyrazol-5-yl]-5-methyl-3-oxo-4-[3-(trifluoromethyl)phenyl]-3,4-dihydropyrazine-2-carboxamide Form A and characterized by having an X-ray powder diffraction pattern comprising specific peaks at 8.0, 15.9 and 17.8° 2θ and wherein said X-ray powder diffraction pattern is measured using CuK$_\alpha$ radiation.

7. A polymorph of a compound according to claim 1, being 6-[1-(4-cyanophenyl)-1H-pyrazol-5-yl]-5-methyl-3-oxo-4-[3-(trifluoromethyl)phenyl]-3,4-dihydropyrazine-2-carboxamide Form A and characterized by having an X-ray powder diffraction pattern comprising specific peaks at 7.4, 8.0, 10.7, 15.9, 16.2, 17.6, 17.8, 21.6, 22.8 and 24.9° 2θ and wherein said X-ray powder diffraction pattern is measured using CuK$_\alpha$ radiation.

8. A polymorph of a compound according to claim 1 being 6-[1-(4-cyanophenyl)-1H-pyrazol-5-yl]-5-methyl-3-oxo-4-[3-(trifluoromethyl)phenyl]-3,4-dihydropyrazine-2-carboxamide Form B.

9. A polymorph of a compound according to claim 1, being 6-[1-(4-cyanophenyl)-1H-pyrazol-5-yl]-5-methyl-3-oxo-4-[3-(trifluoromethyl)phenyl]-3,4-dihydropyrazine-2-carboxamide Form B and characterized by having an X-ray powder diffraction pattern comprising specific peaks at 18.0, 18.2 and 24.7° 2θ and wherein said X-ray powder diffraction pattern is measured using CuK$_\alpha$ radiation.

10. A polymorph of a compound according to claim 1, being 6-[1-(4-cyanophenyl)-1H-pyrazol-5-yl]-5-methyl-3-oxo-4-[3-(trifluoromethyl)phenyl]-3,4-dihydropyrazine-2-carboxamide Form B and characterised by having an X-ray powder diffraction pattern comprising specific peaks at 12.5, 14.3, 14.4, 15.7, 17.5, 18.0, 18.2, 18.8, 22.2 and 24.7° 2θ and wherein said X-ray powder diffraction pattern is measured using CuK$_\alpha$ radiation.

11. A polymorph of a compound according to claim 1 being 6-[1-(4-cyanophenyl)-1H-pyrazol-5-yl]-5-methyl-3-oxo-4-[3-(trifluoromethyl)phenyl]-3,4-dihydropyrazine-2-carboxamide Form C.

12. A polymorph of a compound according to claim 1, being 6-[1-(4-cyanophenyl)-1H-pyrazol-5-yl]-5-methyl-3-oxo-4-[3-(trifluoromethyl)phenyl]-3,4-dihydropyrazine-2-carboxamide Form C and characterized by having an X-ray powder diffraction pattern comprising specific peaks at 7.6, 20.1 and 22.9° 2θ and wherein said X-ray powder diffraction pattern is measured using CuK$_\alpha$ radiation.

13. A polymorph of a compound according to claim 1, being 6-[1-(4-cyanophenyl)-1H-pyrazol-5-yl]-5-methyl-3-oxo-4-[3-(trifluoromethyl)phenyl]-3,4-dihydropyrazine-2-carboxamide Form C and characterized by having an X-ray powder diffraction pattern comprising specific peaks at 7.6, 8.6, 10.7, 12.1, 16.6, 17.1, 20.1, 20.2, 22.7 and 22.9° 2θ and wherein said X-ray powder diffraction pattern is measured using CuK$_\alpha$ radiation.

14. A polymorph of a compound according to claim 1 being 6-[1-(4-cyanophenyl)-1H-pyrazol-5-yl]-5-methyl-3-oxo-4-[3-(trifluoromethyl)phenyl]-3,4-dihydropyrazine-2-carboxamide Form D.

15. A polymorph of a compound according to claim 1, being 6-[1-(4-cyanophenyl)-1H-pyrazol-5-yl]-5-methyl-3-oxo-4-[3-(trifluoromethyl)phenyl]-3,4-dihydropyrazine-2-carboxamide Form D and characterized by having an X-ray powder diffraction pattern comprising specific peaks at 7.4, 10.6 and 18.2° 2θ and wherein said X-ray powder diffraction pattern is measured using CuK$_\alpha$ radiation.

16. A polymorph of a compound according to claim 1, being 6-[1-(4-cyanophenyl)-1H-pyrazol-5-yl]-5-methyl-3-oxo-4-[3-(trifluoromethyl)phenyl]-3,4-dihydropyrazine-2-carboxamide Form D and characterized by having an X-ray powder diffraction pattern comprising specific peaks at 7.4, 10.6, 17.3, 18.2, 18.5, 21.4, 22.8, 23.1, 24.8 and 24.9° 2θ and wherein said X-ray powder diffraction pattern is measured using CuK$_\alpha$ radiation.

17. A polymorph of a compound according to claim 1 being 6-[1-(4-cyanophenyl)-1H-pyrazol-5-yl]-5-methyl-3-oxo-4-[3-(trifluoromethyl)phenyl]-3,4-dihydropyrazine-2-carboxamide Form E.

18. A polymorph of a compound according to claim 1, being 6-[1-(4-cyanophenyl)-1H-pyrazol-5-yl]-5-methyl-3-oxo-4-[3-(trifluoromethyl)phenyl]-3,4-dihydropyrazine-2-carboxamide Form E and characterized by having an X-ray powder diffraction pattern comprising specific peaks at 7.4, 10.1 and 19.0° 2θ and wherein said X-ray powder diffraction pattern is measured using CuK$_\alpha$ radiation.

19. A polymorph of a compound according to claim 1, being 6-[1-(4-cyanophenyl)-1H-pyrazol-5-yl]-5-methyl-3-oxo-4-[3-(trifluoromethyl)phenyl]-3,4-dihydropyrazine-2-carboxamide Form E and characterized by having an X-ray powder diffraction pattern comprising specific peaks at 6.9, 7.4, 10.1, 14.7, 15.0, 15.7, 16.4, 19.0, 19.3 and 22.5° 2θ and wherein said X-ray powder diffraction pattern is measured using CuK$_\alpha$ radiation.

* * * * *